(12) United States Patent
Miller et al.

(10) Patent No.: US 7,674,588 B2
(45) Date of Patent: Mar. 9, 2010

(54) SCREENING USING POLARIZATION ANISOTROPY IN FRET EMISSIONS

(75) Inventors: Steven C. Miller, Union City, CA (US); Paul B. Comita, Menlo Park, CA (US); Christopher B. Shumate, Carlsbad, CA (US); Evan F. Cromwell, Redwood City, CA (US)

(73) Assignee: Blueshift Biotechnologies, Inc., Sunnyvale, CA (US)

(*) Notice: Subject to any disclaimer, the term of this patent is extended or adjusted under 35 U.S.C. 154(b) by 0 days.

(21) Appl. No.: 12/069,724

(22) Filed: Feb. 11, 2008

(65) Prior Publication Data

US 2008/0206888 A1 Aug. 28, 2008

Related U.S. Application Data

(63) Continuation of application No. 11/398,496, filed on Apr. 4, 2006, now abandoned.

(60) Provisional application No. 60/678,842, filed on May 6, 2005, provisional application No. 60/668,428, filed on Apr. 4, 2005.

(51) Int. Cl.
  *C12Q 1/68* (2006.01)
  *G01N 33/53* (2006.01)
  *C07H 21/02* (2006.01)
  *C07H 21/04* (2006.01)

(52) U.S. Cl. ........................ 435/6; 536/23.1; 536/24.3

(58) Field of Classification Search ................ 435/6, 435/7.1; 536/23.1, 24.3
See application file for complete search history.

(56) References Cited

U.S. PATENT DOCUMENTS

| | | | |
|---|---|---|---|
| 5,597,696 A | 1/1997 | Linn et al. | |
| 5,807,522 A | 9/1998 | Brown et al. | |
| 6,509,161 B1 | 1/2003 | Barker et al. | |
| 6,713,262 B2 | 3/2004 | Gellibolian et al. | |
| 2003/0059811 A1 | 3/2003 | Djaballah et al. | |
| 2003/0228603 A1 | 12/2003 | Cload et al. | |
| 2003/0228703 A1 | 12/2003 | Hoppe et al. | |
| 2005/0009174 A1* | 1/2005 | Nikiforov et al. | 435/287.2 |
| 2006/0160111 A1 | 7/2006 | Piston et al. | |
| 2008/0206888 A1* | 8/2008 | Miller et al. | 436/501 |
| 2008/0225906 A1* | 9/2008 | Ishihara et al. | 372/24 |

FOREIGN PATENT DOCUMENTS

WO WO 2006/010839 2/2006

OTHER PUBLICATIONS

Gautier et al., Homo-FRET Microscopy in living cells to measure monomer-dimer transition of GFP-tagged proteins. Biophysical Joiurnal 80: 3000-3008 (2001).*
Squire et al., Red-edge anistropy microscopy enables dynamic imaging of homo-FRET between green fluorescent proteins in cells. J. of Structural Biology 147: 62-69 (2004).*
Tramier et al., Homo-FRET versus hetero-Fret to probe homodimers in living cells. Methods in Enzymology 360 : 580-597(2003).*
International Search Report dated May 4, 2006 from related International Application No. PCT/US05/23520.
Mere et al., "Miniaturized FRET assays and microfluidics: key components for ultra-high-throughput screening,"Aug. 1999, vol. 44, No. 8, DDT.
Gonzalez et al., Cellular Fluorescent Indicators and Voltage/Ion Probe Reader (VIPR™): Tools for Ion Channel and Receptor Drug Discovery, Taylor & Francis healthsciences, Receptors and Channels, 8:283-295, 2002.
International Search Report dated Sep. 6, 2006 from International Application No. PCT/US06/12292.
Lidke et al., "Imaging Molecular Interactions in Cells by Dynamic and Static Fluorescence Anisotropy (fRLIM and emFRET)," Biochemical Society Transactions, vol. 31, Part 5, pp. 1020-1027, 2003.
John C. Owicki, "Fluorescence Polarization and Anisotropy in High Throughput Screening: Perspectives and Primer," Journal of Biomolecular Screening, vol. 5, No. 5, pp. 297-306, 2000.
Office Action dated Aug. 10, 2007 from related U.S. Appl. No. 11/398,496.

(Continued)

*Primary Examiner*—Ethan Whisenant
(74) *Attorney, Agent, or Firm*—Weaver Austin Villeneuve & Sampson LLP

(57) ABSTRACT

Methods and apparatus are described for detecting specific binding between first and second chemical entities. The first chemical entity in association with a first fluorophore is immobilized. The second chemical entity is allowed to bind with the immobilized first chemical entity. The second chemical entity is or becomes coupled to a second fluorophore, which forms a FRET pair with the first fluorophore. The bound chemical entities are exposed to radiation at an excitation frequency for either the first or the second fluorophore, and polarization anisotropy of a FRET fluorescent signal from the bound chemical entities is measured to detect specific binding between the first and second chemical entities. Techniques are also disclosed for detecting whether a FRET interaction is occurring between a first chemical entity including a donor fluorophore and a second chemical entity including an acceptor fluorophore, using simultaneous anisotropy measurements at the wavelengths of the donor and acceptor fluorophores.

36 Claims, 18 Drawing Sheets

OTHER PUBLICATIONS

Zal et al., "Using live FRET imaging to reveal early protein-protein interactions during T cell activation", *Current Opinion In Immunology*, vol. 16, No. 4, Aug. 1, 2004, pp. 418-427.

Rizzo et al., "High-contrast imaging of fluorescent protein FRET by fluorescence polarization microscopy", *Biophysical Journal*, vol. 88, No. 2, Feb. 1, 2005, pp. L14-L16.

Mattheyses et al., "Polarized Fluorescence Resonance Energy Transfer Microscopy", *Biophysical Journal*, vol. 87, No. 4, Oct. 1, 2004, pp. 2787-2797.

Lichlyter et al., "Development of a novel FRET immunosensor technique", *Biosensors & Bioelectronics*, vol. 19, No. 3, Nov. 30, 2003, pp. 219-226.

Singh et al., "Fluorescence Polarization For Monitoring Ribozyme Reactions In Real Time", *Biotechniques*, vol. 29, No. 2, Aug. 1, 2000, pp. 344-351.

Search Report dated Mar. 10, 2009 for European Patent Application No. 06758259.3.

Office Action dated Jul. 7, 2009 for European Patent Application No. 06758259.3.

\* cited by examiner

Spot array format for protein phosphorylation screening by FRET

Spot array format for protein phosphorylation screening by FRET

SCREENING USING POLARIZATION ANISOTROPY IN FRET EMISSIONS

CROSS REFERENCE TO RELATED APPLICATIONS

This application is a continuation of U.S. application Ser. No. 11/398,496, filed on Apr. 4, 2006 now abandoned, and entitled "SCREENING USING POLARIZATION ANISOTROPHY IN FRET EMISSIONS", which claims benefit of U.S. Provisional Patent Application No. 60/668,428, filed Apr. 4, 2005, and entitled "IN VITRO SCREENING USING POLARIZATION ANISOTROPY IN FRET EMISSIONS," and of U.S. Provisional Patent Application No. 60/678,842, filed May 6, 2005, and entitled "SIMULTANEOUS TWO-COLOR DIFFERENTIAL ANISOTROPY IN FRET ASSAYS." All of these applications are hereby incorporated by reference herein for all purposes.

BACKGROUND

This invention relates to improved Fluorescence Resonant Energy Transfer (FRET) techniques for use in high speed miniaturized assays for solutions, as well as in object-based and cell-based fluorimetry assays.

FRET provides an indication of proximity between donor and acceptor fluorophores. When a donor is excited with incident radiation at a defined frequency, some of the energy that the donor would normally emit as fluorescence is transferred to the acceptor, when the acceptor is in sufficiently close proximity to the donor (typically, within about 50 Angstroms for most donor fluorophores). At least some of the energy transferred to the acceptor is emitted as radiation at the fluorescence frequency of the acceptor. FRET is further described in various sources, such as "FRET Imaging" (Jares-Erijman, E. A, and Jovin, T. M, Nature Biotechnology, 21(11), (2003), pg 1387-1395), which is incorporated herein by reference for all purposes.

Another important concept in the context of this invention is anisotropy. Anisotropy provides a measure of the degree to which radiation is non-randomly polarized; that is, the degree to which one polarization orientation predominates over its orthogonal polarization orientation. A highly anisotropic signal will be highly polarized (for example, purely linearly polarized). A highly isotropic signal approaches random polarization. In one conventional approach, anisotropy (r) is calculated using the following equation:

$$r = \frac{VV - gVH}{VV + 2gVH}$$

where VH and VV are the horizontal and vertical emission polarizations relative to a vertical excitation polarization and g corrects for polarization bias of the optical instrument.

Traditionally, FRET analysis relies on detecting one or more of the following: (1) the presence of fluorescence at the emission frequency of the acceptor, (2) the ratio of acceptor to donor fluorescence intensities, and (3) the lifetime of the donor's fluorescent emission. Each of these techniques has attendant difficulties. For example, merely detecting the presence of fluorescence at the emission frequency of the acceptor typically is not sufficient because the acceptor will produce some natural fluorescence when exposed to the frequency used to excite the donor fluorophore. Furthermore, time-resolved FRET imaging and analysis requires more complex instrumentation than standard fluorescence imaging and analysis.

Polarization anisotropy has been proposed as a FRET detection technique. Fluorescence generated from a FRET acceptor fluorophores is depolarized from the FRET process, and generally has relatively lower anisotropy than the fluorescence generated directly from donor fluorophores. Thus, anisotropy can be used as a measure of FRET, and, consequently, the associated proximity of donor and acceptor fluorophores. The use of this technique in homo-FRET, or FRET between like fluorophores, has been described in "Imaging molecular interactions in cells by dynamic and static fluorescence anisotropy (rFLIM and emFRET)" (Lidke, D. S., Nagy, P., Barisas, B. G., Heintzmann, R., Post, J. N., Lidke, K. A., Clayton, A. H. A., Arndt-Jovin, D. J. and Jovin, T. M., Biochem. Soc. Trans., 31(5) (2003), pg. 1020-1027), which is incorporated herein by reference for all purposes.

Fluorescence anisotropy can also be employed as a FRET detection strategy in living cells. As has been described in "High contrast imaging of fluorescent protein FRET by fluorescence polarization microscopy" (Rizzo, M. A. & Piston, D. W., Biophys J, 88 L14-16,2005), the fluorescence anisotropy for mCerulean, a type of Cyan Fluorescent Protein (CFP), has a value of about 0.3 across its entire wavelength emission range. However, when the mCerulean is in a FRET pair with mVenus, a type of Yellow Fluorescent Protein (YFP), the anisotropy remains high (slightly above 0.3) when the fluorescence is emitted by the donor (that is, the mCerulean) and decreases to about 0.15 when the fluorescence is emitted by the acceptor (that is, the mVenus). Although difference in anisotropy is very consistent between different measurements, the difference is relatively small and has limited use in experimental situations, since there are typically many unknowns and calibration factors which may affect the change in anisotropy. Thus it would be desirable to have, inter alia, an improved and more reliable method of measuring anisotropy changes associated with the FRET process.

SUMMARY

One aspect of the invention pertains to methods and apparatus for detecting specific binding between a first chemical entity and a second chemical entity. The first chemical entity in association with a first fluorophore may be immobilized. The second chemical entity is allowed to bind with the immobilized first chemical entity. The second chemical entity is or becomes coupled to a second fluorophore, which forms a FRET pair with the first fluorophore. The bound chemical entities are exposed to radiation at an excitation frequency for either the first or the second fluorophore, and polarization anisotropy of a FRET fluorescent signal from the bound chemical entities is measured to detect specific binding between the first and second chemical entities.

Advantageous implementations can include one or more of the following features. In some cases, information in addition to anisotropy can be employed to evaluate a sample. For example, the method may include measuring donor emission lifetime of at least one of the first or second fluorophores. In some cases, the method measures the relative or absolute intensities of one or both fluorophores. In certain embodiments, the first and second fluorophores are the same (homo-FRET).

Many different chemical entities are contemplated for use with this invention. These may be small molecules, complexes, biomolecules such as proteins and nucleic acids, assemblies of molecules, biological structures such as organelles, etc. In certain embodiments, one of the first and second chemical entities comprises a protein and the other of the first and second chemical entities comprises a nucleic acid. In some embodiments, the method comprises performing a defined treatment on at least one of the first and second chemical entities, such that specific binding between the first and second chemical entities only occurs when the defined treatment results in at least one of the first and second chemical entities entering a particular state (e.g., a conformational state, a chemical modification such as phosphorylation, etc.).

Note that depending on the assay design, the polarization anisotropy may be measured at a single wavelength or multiple wavelengths. More typically, the fluorophores will be different. In some embodiments, the anisotropies of first and second wavelengths are measured simultaneously. In some embodiments, the anisotropies of the first and second wavelengths are measured sequentially in a time frame that is short with respect to a systematic measured change in signal readout. An example of a systematic measured change is biomolecular transition in a cascade of reactions in a biochemical pathway. The assay is designed to measure the biomolecular transition.

Another aspect of the invention pertains to methods and apparatus for detecting whether a FRET interaction is occurring between a first chemical entity including a donor fluorophore and a second chemical entity including an acceptor fluorophore. The chemical entities are exposed to radiation at an excitation wavelength for the first fluorophore. A polarization anisotropy of a fluorescent signal from the chemical entities is measured at an emission wavelength for the donor fluorophore and at an emission wavelength for the acceptor fluorophore. The measured anisotropies are compared to determine whether a FRET interaction is occurring between the first and second chemical entities. The anisotropy of signal at the emission wavelength for the donor fluorophore may provide an internal reference for calibrating the anisotropy measured at emission wavelength for the acceptor fluorophore. In other embodiments, the anisotropy of the emission wavelength for the acceptor fluorophore is compared with an "external" reference such as the anisotropy of the excitation source radiation or a separate fluorophore, unconnected with the FRET pair, which is provided in the assay sample. In the latter example, the external reference may be provided by, for example, a bead or a spot of fluorophore provided within or proximate to the sample.

Advantageous implementations can include one or more of the following features. In certain embodiments, a FRET interaction is determined to occur when the measured anisotropy at the emission wavelength of the acceptor fluorophore changes relative to the measured anisotropy at the emission wavelength of the donor fluorophore. In some cases, the anisotropies of the donor fluorophore and acceptor fluorophore are measured simultaneously. In certain embodiments, the anisotropies of the first and second wavelengths are measured sequentially in a time frame that is short with respect to a systematic measured change in signal readout.

The first and second chemical entities may be included in a target region for FRET analysis. Examples of target regions include one or more of microbeads, spots, spot on spot, spot on a slide combined with a bead, samples or objects confined in a capillary tube, samples or objects confined in a microfluidic channel, aggregates or colonies of cells confined in a liquid region such as a well or droplet, and aggregates or colonies of cells immobilized on a surface or surface layer.

Many different types of interactions may be compared using methods of this invention. In one example, at least one of the chemical entities is a small molecule that becomes loses some conformation flexibility upon binding to the other chemical entity. Many different fluorophore combinations may be employed. In some cases, the donor fluorophore and the acceptor fluorophore are the same. The chemical entities may be associated with fluorophores in many different ways. In one example a conventional binding mechanism is employed such as an antibody-antigen interaction or a strepavidin-biotin interaction.

The invention can be implemented to include one or more of the following advantages. Using array-based assays in which polarization anisotropy in FRET is employed to detect specific binding does not require time-based signal capture and does not require collection at multiple wavelengths (that of the donor and acceptor fluorophore emissions), unless two-color anisotropy measurements are made on the array-based assays. It also provides a large dynamic range and high signal to noise ratio. FRET-based assays of this invention can be utilized in essentially any currently available assay format, including various types of sandwich assays. The assays may be employed to detect biological molecules as well as various non-biological molecules such as chemical warfare agents. The conventional assays are simply modified so that binding partners are each supplied with their own fluorophore, one being a donor fluorophore and the other being an acceptor fluorophore.

The details of one or more embodiments of the invention are set forth in the accompanying drawings and the description below. Other features and advantages of the invention will be apparent from the description and drawings, and from the claims.

DESCRIPTION OF DRAWINGS

Like reference symbols in the various drawings indicate like elements.

DETAILED DESCRIPTION

Figure 1:
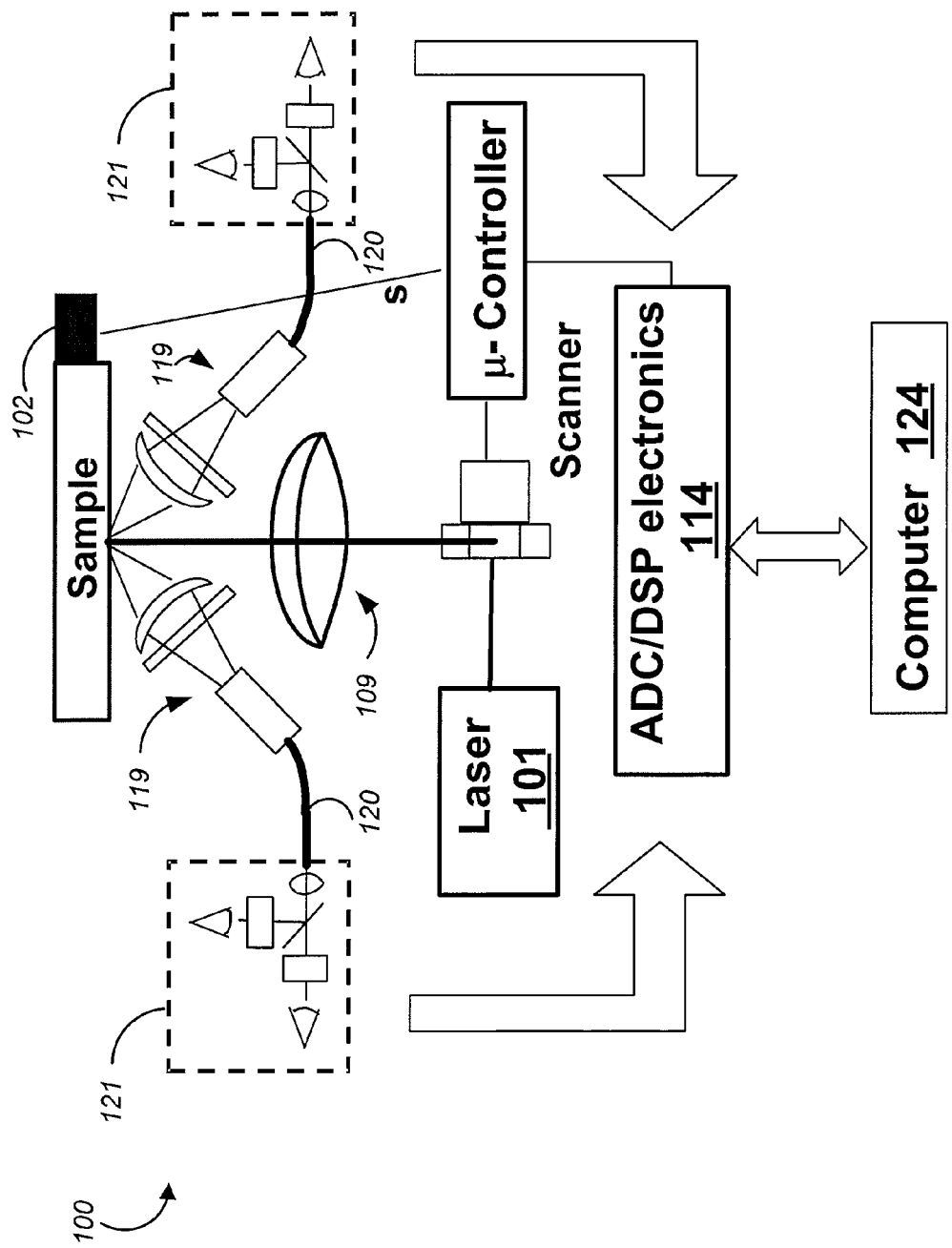
FIG. 1 shows a schematic block diagram of an apparatus that can be used for FRET analyses in accordance with the invention.

In accordance with one aspect of the present invention, anisotropy is measured as part of a FRET detection strategy in assays, such as the mentioned array-based assays, to detect specific binding. In accordance with another aspect of the present invention, the invention provides methods and apparatus, implementing and using techniques for improved FRET detection and/or quantization, generally, as well as in the above-mentioned array-based assays.

The improved FRET detection techniques stem from the realization that a dye that functions as an acceptor in a FRET pair has significantly lower anisotropy than it has when it is not interacting in a FRET pair. A dye that functions as a donor in a FRET pair, however, has essentially the same anisotropy when it is the donor in a FRET pair and when it is not interacting as a donor in a FRET pair. Thus, by studying the ratio or difference between the anisotropy in the emission wavelength region of the acceptor and the emission wavelength region of the donor, it is possible to determine whether FRET interaction is occurring. Furthermore, the anisotropy of the donor's emission can work as an internal reference against which the anisotropy change of the acceptor's emission can be detected and/or quantified. In certain embodiments, apparatus in accordance with the invention allows simultaneous anisotropy measurements to be performed in two different wavelength regions. Thereby, both types of anisotropy are measured while all other parameters remain the same, which avoids any uncertainty that parameters might have changed, as would be the case if sequential measurements were performed. Furthermore, the apparatus allows the measurements and processing to be done in real time at the time of detection and subsequent digitization. This is referred to below as either "streaming data processing" or "on-the-fly" data processing.

Specific embodiments of the invention are described in detail below and illustrated in the accompanying drawings. While the invention will be described in conjunction with these specific embodiments, it will be understood that they are not intended to limit the invention to one embodiment. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Many different types of instrumentation are suitable for analyzing anisotropy in arrays employing FRET systems to identify specific binding. A description of some suitable apparatus is provided in the following documents: U.S. patent application Ser. No. 10/927,748 (Published Application No. 2005-0046848-A1, published Mar. 3, 2005), filed Aug. 26, 2004, Entitled: Time Dependent Fluorescence Measurements, by inventors Cromwell et al., U.S. patent application Ser. No. 10/928,484 (Published Application No. 2005-0046849-A1, published Mar. 3, 2005), filed Aug. 26, 2004, Entitled: Measuring Time Dependent Fluorescence, by inventors Cromwell et al. and U.S. patent application Ser. No. 11/055,244, filed Feb. 9, 2005, Entitled: Methods And Apparatus For Scanning Small Sample Volumes, each of which is incorporated herein by reference for all purposes.

FIG. 1 shows a schematic diagram of one embodiment of an apparatus (100) suitable for detecting anisotropy in a sample. The operation of comparable apparatus has been described in detail in the above-referenced patent applications. In brief, the sample sits on a translation stage (102) and is excited by a laser (101) through a set of optical elements (109). The optical elements focus the light from the laser (101) onto a region of the sample to be imaged. The focal region is located above, for example, a base of a microarray plate. The sample can be objects to be interrogated by fluorescence, such as cells or immobilized members of an in vitro binding pair attached to the bottom of a microwell of the microarray plate.

The resulting fluorescence from the sample is collected with two sets of collection optics (119) and passed to two respective detectors (121). The collection optics (119) can be configured to allow scanning of a large array, such as a microarray plate. In one embodiment, the collection optics (119) is a rod lens, designed to capture the entire range of sweep of the beam over one dimension of the base of the sample array. The collection optics (119) can also include other types of lenses, or an aggregate of lenses, as would be chosen for a particular assay type to capture the specific information required from the emission in such assay. In some embodiments, multiple setups of collection optics (119) can be used to improve collection efficiency.

The two sets of collection optics (119) allow simultaneous collection of separate components of emitted fluorescent light (e.g., separate wavelengths, polarization states, etc.). For example, a first polarizing filter can be used to pass only light of a first polarization to a first detector, and a second polarizing filter can be used to pass only light of a second, orthogonal, polarization to a second detector. The correlation of the signals collected in this configuration, detection in the detection system, and subsequent manipulation of the stored signal give rise to information not available to a single detector, with attendant improvement in signal. Thus, the information derived from this apparatus is steady-state anisotropy. Furthermore, when the apparatus is configured with appropriate detection circuitry to capture fluorescence lifetime data, it is possible to measure the correlation of time-dependent behavior of fluorescence anisotropy. As will be discussed in further detail below, this anisotropy measurement capability can be advantageously used to provide important information in FRET measurements.

The transmission of the fluorescent light to the detectors (121) can be accomplished by, for example, an optical fiber or a bundle of optical fibers (120). In one embodiment, the detectors (121) are detectors with high gain, such as photomultiplier tubes, which produce electrical output signals. It should be noted that any polarization filtering is typically performed before the collected light enters any optical fibers (120), since most optical fibers distort the polarization information and light that is output from an optical fiber does not have identical polarization components to the light that was input to the optical fiber at the other end. In the depicted embodiment, the output signals from the detectors are processed by ADC/DSP electronics (114) and passed on to a computer (124) for further processing. The computer (124) performs operations such as optimization of the gain and the signal to noise ratio (S/N), by making use of signal enhancing, averaging, or integrating detection systems.

In certain embodiments, the FRET detection apparatus can be very simple; it need only be outfitted to measure the polarization state of emitted radiation. However, more complex instrumentation may be employed to provide additional data relevant to FRET. For example, the instrumentation may also be capable of measuring the lifetime of fluorescent signals, particularly intensity as a function of time and/or anisotropy as a function of time. In a typical system, the detection circuitry is capable of recording and storing an emission signal (or multiple emission signals at different wavelengths) for a period of between about 0.5 nanoseconds and 10 nanoseconds after the excitation energy is removed from the sample. In some cases, depending upon the fluorophore employed, the measured duration of the emission signal may be in the hundreds of nanoseconds or even microseconds. Certain rare earth doped fluorophores have fluorescence lifetimes in the millisecond range. As indicated above, one manifestation of FRET is a reduced donor emission lifetime. The instrumentation may also have the ability to simultaneously capture emitted radiation at the frequencies of both the donor and the acceptor, or acceptor and some other reference radiation source with a known anisotropy. This allows the instrument to provide intensity ratio measurements as well. The above apparatus may be outfitted with redundant collectors for the different frequencies or it may employ a single collection system that alternately captures radiation at a reference frequency and a signal frequency.

As explained in more detail elsewhere herein, certain embodiments of the invention employ a reference signal to calibrate FRET signals, particularly the anisotropy, lifetime, and/or intensity of such signals. In many cases, the reference signal will be an internal reference taken from, for example, emission of a donor fluorophore in the FRET pair.

More generally, the internal reference for measurement may be provided from a molecular fluorophore having similar physical and/or chemical properties to the fluorophore in the sample whose signal is being measured (i.e., the acceptor fluorophore). This source of internal reference is often desirable because the physico/chemical interaction present in the reference fluorophore will presumably be acting in the same way as in the sample itself. Therefore, the analogous molecular internal reference provides an accurate internal calibrated reference polarization source. However, there may be circumstance where such reference signal may not be as advantageous to use. In such cases, an alternative reference source such as signal from the excitation source itself (e.g., a laser) is a suitable internal reference because it provides a particularly strong signal and is not dispersed among many wavelengths as the fluorescence signal normally is. Such reference signal can easily be measured in a scatter channel, and is not depolarized except by way of the measurement optics. In a similar way, for a spot array, a reference fluorophore can be spotted and made large and highly concentrated, so the fluorescence reference signal is very strong and easy to measure.

Another instance where an external reference may be desirable is the case where the internal reference chromophore undergoes homo-FRET, and this causes the internal anisotropy to become depolarized. In this case the internal reference may not be reliable, or may be systematically changing with conditions such as concentration, etc. So in this case an external reference may be more reliable, especially one that provides a strong signal that is present with the sample.

Anisotropy readouts of the FRET process may be advantageously employed in conventional array-based assays, such as ELISA, particularly those that suffer from high levels of non-specific binding. Such non-specific binding may occur at locations on a ligand other than the specific binding site of interest, producing background signal that interferes with analysis. For example, an analyte species sometimes attach to the Fc domain, rather than the variable domain, of an immobilized antibody, thereby providing a false indication of specific binding. By employing a FRET detection strategy, non-specific binding contributes relatively little to the collected signal and therefore does not significantly interfere with detection. Only those array locations where the donor and acceptor fluorophores are held in close proximity (typically the locations where specific binding has occurred) generate signal. As a result, FRET-based assays can provide improved signal-to-noise ratio over conventional array-based assays. However, the potential of FRET as an array-based detection technique has not been realized because of, for example, complicated instrumentation. Embodiments of the present invention provide array-based assays in which polarization anisotropy in FRET is used to detect specific binding.

FIGS. 2-6 present a small sampling of available assay formats that may be employed in implementations of the present invention. Each format employs an in-vitro assay in which a FRET pair forms when a binding event of interest occurs. The FRET pairing is detected using high throughput polarization anisotropy.

In the examples presented in these figures, the protein-protein interaction detectable by FRET anisotropy takes place only when a residue (for example, tyrosine) is phosphorylated. Such phosphorylation may occur, for example, during signal transduction within a cell. Assays as depicted in the figures can provide information about the effects of various stimuli on the portion of the signal pathway involving tyrosine phosphorylation. For example, a particular treatment under investigation may possibly interfere with a kinase's ability to phosphorylate tyrosine in a protein involved in the signal pathway.

Of course, the invention is not limited to detecting interactomes (interaction features in a signal pathway) or any other class of reactions or molecular features. The assays of this invention can be applied to essentially any small dimension morphological or molecular feature. Features that can be assayed include protein domains, nucleic acid sequences, epitopes, various complexes, trascriptomes, and interactomes. The structure, physical and/or chemical features of essentially any chemical or biochemical species or moiety can be assayed. This includes protein-protein interactions, protein-nucleic acid interactions, and nucleic acid-nucleic acid interactions. Some examples of protein array assays are described in Zhu, Bilgin, and Snyder, "Proteomics", Annu. Rev. Biochem. 16 (2003), pages 783-812, which is incorporated herein by reference for all purposes.

Figure 2:
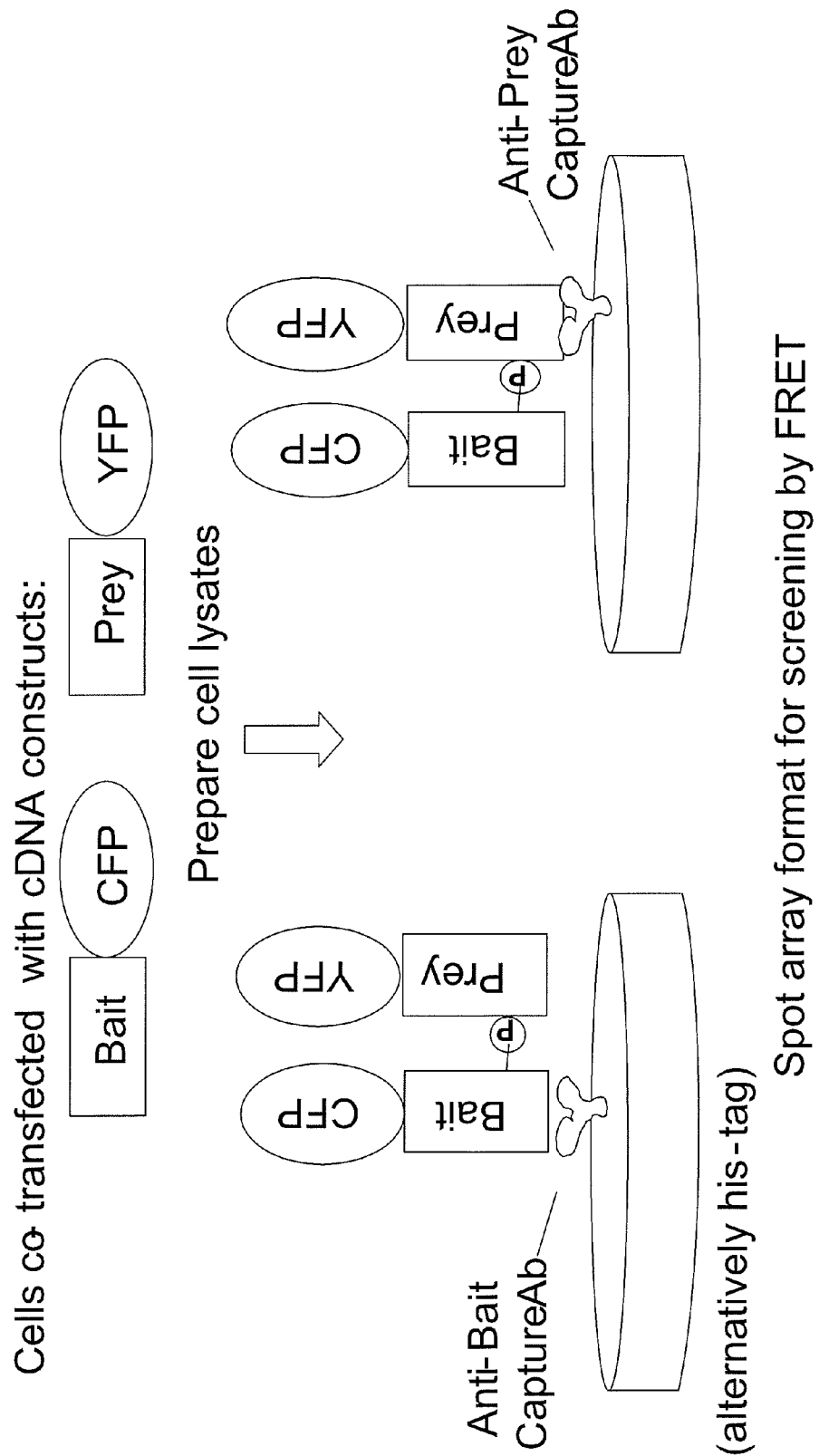
FIG. 2 shows an assay design for determining whether experimental conditions have affected a "bait" protein in a particular way, in accordance with one embodiment of the invention.

FIG. 2 shows an assay design for determining whether experimental conditions have affected a "bait" protein in a particular way (phosphorylated tyrosine in this example). One way to conduct the experiment is to prepare cells cotransfected with two cDNA constructs, one for the bait protein coupled to a first fluorophore (e.g., CFP (Cyan Fluorescent Protein)) and the other for a "prey" protein coupled to a second fluorophore (e.g., YFP (Yellow Fluorescent Protein)). Of course the applied fluorescent proteins could be switched between bait and prey and/or other cellular components under investigation or could be modified via cDNA constructs or in other manners to permit attachment of the FRET pair fluorophores.

In a typical experiment, the transfected cells are exposed to a particular stimulus under investigation (for example, a pharmaceutical candidate) and allowed to grow. The cells are then lysed and the cellular contents are assayed, in some cases after being subjected to an initial separation procedure. In the example of FIG. 2, left side, the lysate is contacted with a substrate having immobilized anti-bait capture antibodies. In another embodiment, his-tags may be employed to capture the bait. If the experimental conditions have modified the bait in a way that allows coupling with the prey (for example, the bait has been appropriately phosphorylated), then the captured bait and its associated prey will be effectively bound in close proximity on the substrate. As a consequence the FRET pair, CFP and YFP in this example, will be sufficient close to allow resonant energy transfer. Using a polarization anisotropy detection instrument, FRET can be detected as described above. The degree of anisotropy will indicate, indirectly, that the bait has undergone a modification under investigation. The right side of FIG. 2 shows a similar example, except that here the immobilized antibody binds to the prey rather than the bait. The end result is still the same: the FRET pair is locally immobilized and detectable on the substrate.

Figure 3:
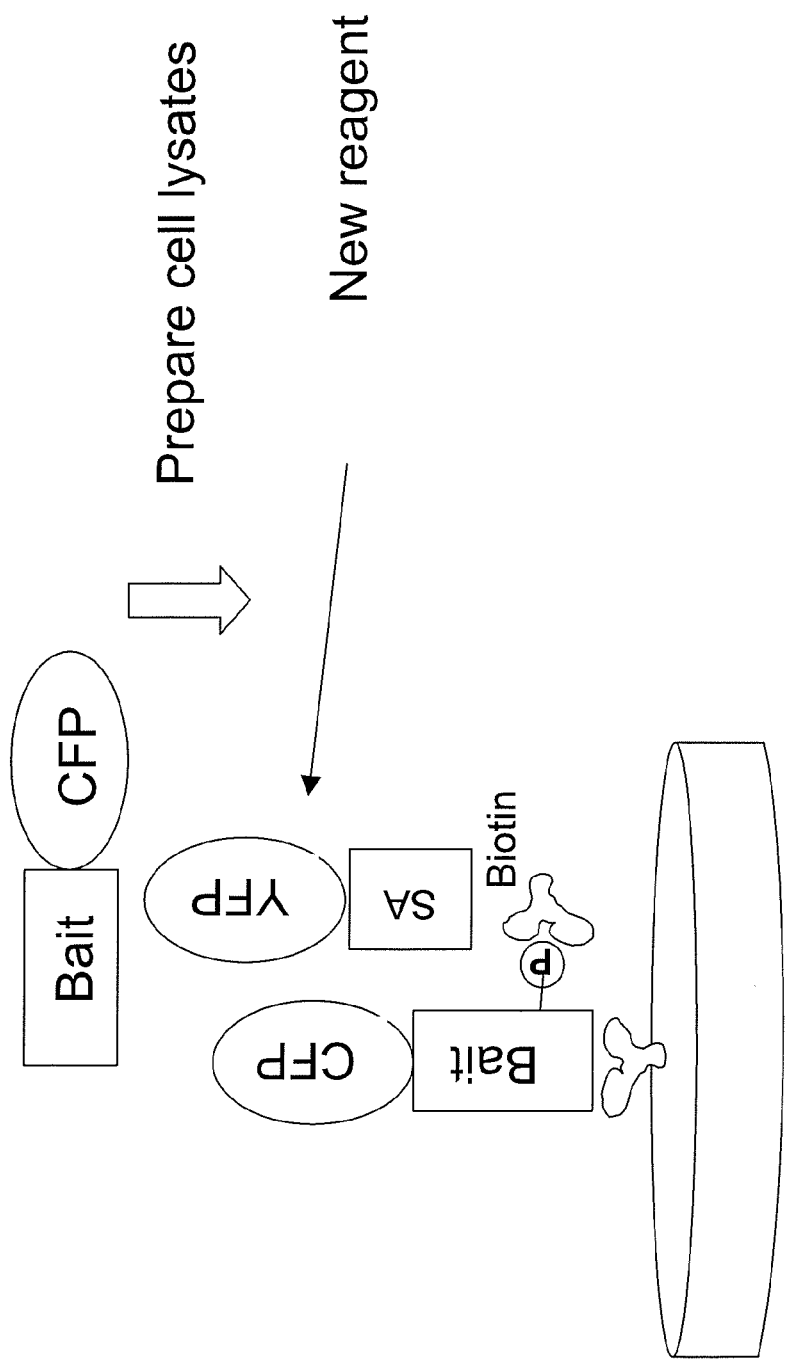
FIG. 3 illustrates a similar experimental protocol and related assay to the one depicted in FIG. 2, with cells transfected with only a bait-fluorophore cDNA construct.

FIG. 3 illustrates a similar experimental protocol and related assay. However, in this case, cells are transfected with only the bait-fluorophore cDNA construct. The same experimental conditions may be applied; for example, conditions that will affect whether the bait is modified in a particular manner (e.g., phosphorylated). At the appropriate time, the cells are lysed and the lysate is exposed to a solid substrate having affixed anti-bait antibodies. The substrate is then exposed to a new reagent comprised of (1) an antibody that is selective for the modified protein (for example, selective for a particular protein domain having a phosphorylated tyrosine residue) and (2) a fluorophore that serves as a partner for the bait fluorophore in FRET pair. The antibody and the fluorophore in the new reagent may be linked by any of many available linking techniques. A biotin-streptavidin pair is shown in FIG. 3.

Figure 4:
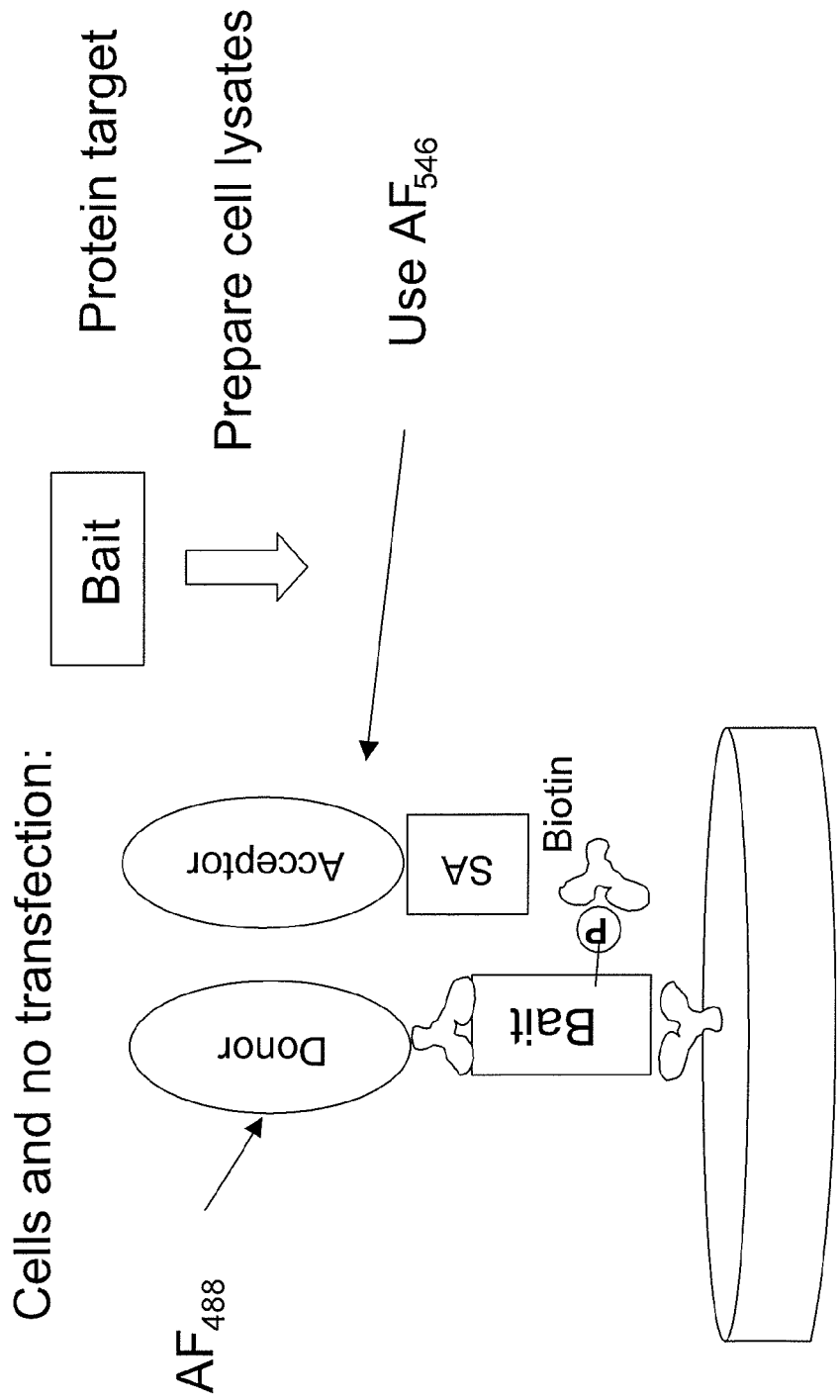
FIG. 4 shows another variation on the assays presented in FIGS. 2 and 3.

FIG. 4 shows another available variation on the assays. In this case, the cells need not be transfected with a cDNA construct for the bait and a fluorophore. Rather, the fluorophore is attached to the bait after lysing, and possibly after the bait attaches itself to the substrate through the affixed anti-bait antibody. In the depicted example, a generic donor fluorophore couples to the bait protein through another anti-bait antibody to form a sandwich structure as shown. Because the cells are not transfected, the fluorophore need not be compatible with living cells. In a specific example, the FRET fluorophore pair includes Alexa Fluor 488 and Alexa Fluor 546 available from Invitrogen Corporation of Carlsbad, Calif.

Figure 5:
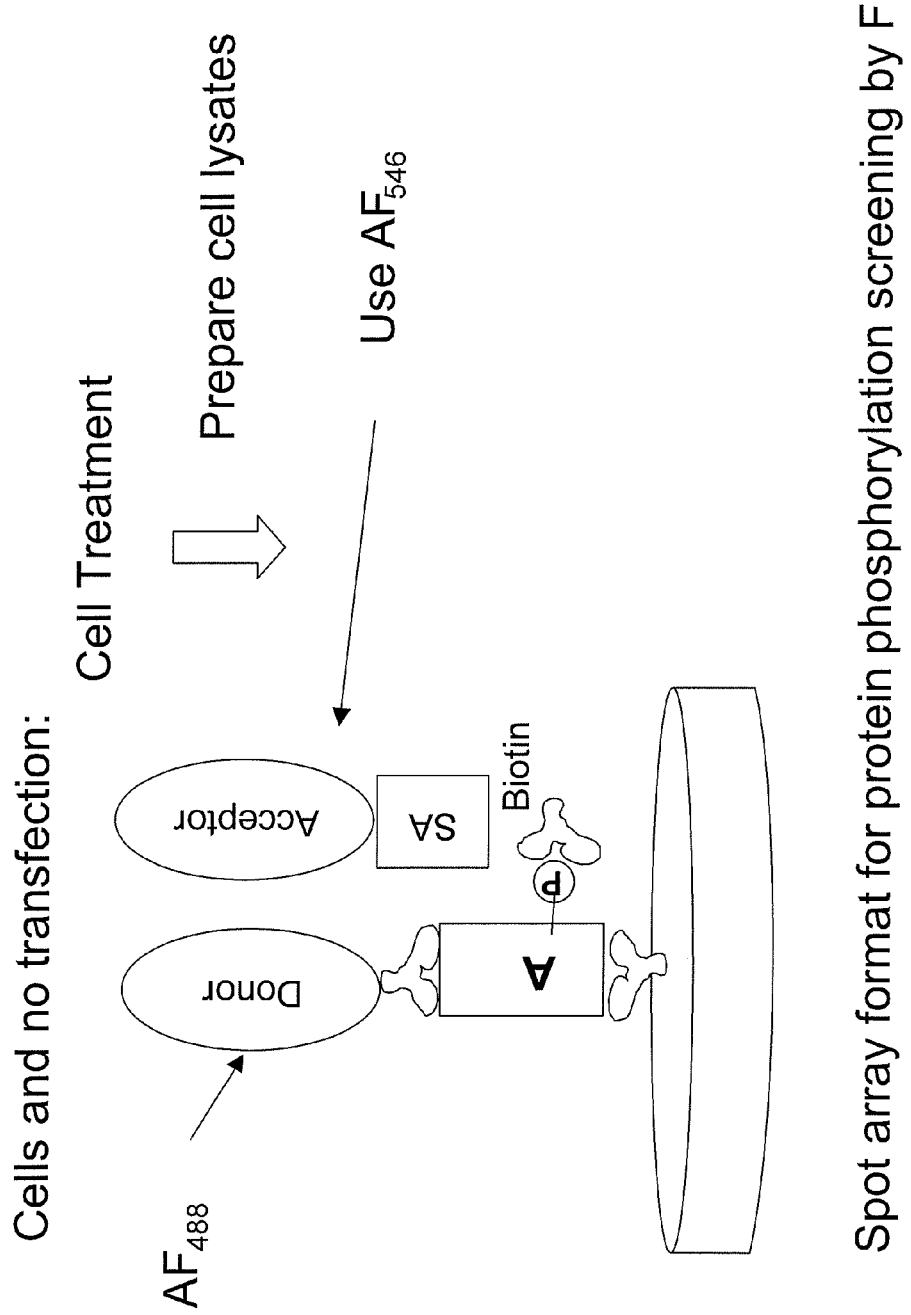
FIG. 5 illustrates a generic version of the assay depicted in FIG. 4.

FIG. 5 presents a generic version of the assay depicted in FIG. 4, in which the species under investigation need not be a "bait" protein. Essentially any protein or other species "A" can be detected using assays of this invention.

Figure 6:
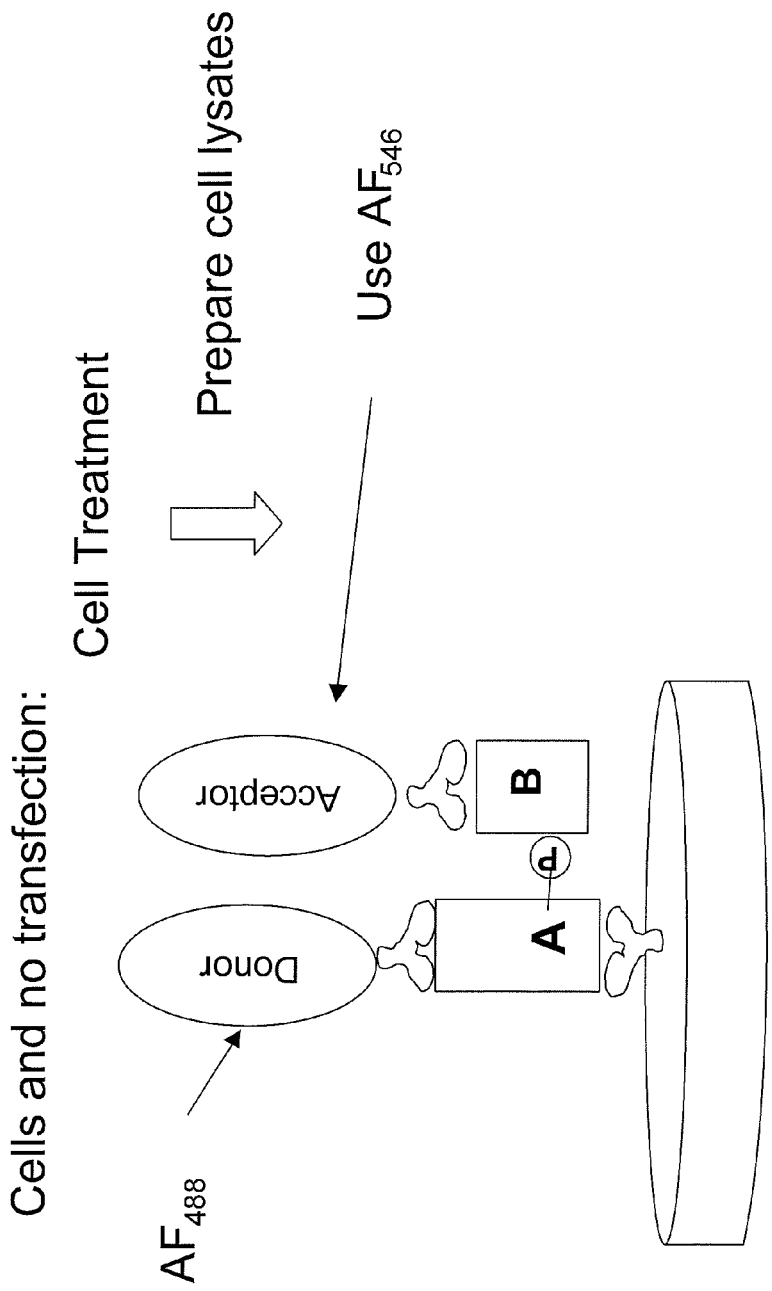
FIG. 6 shows an extension of the assays in FIGS. 2-5 to detection of agents using specific binding mechanisms.

FIG. 6 shows that the assays of FIGS. 1 through 4 can be extended to situations in which the feature of interest (for example, phosphorylated tyrosine at a particular residue position) can be detected by many different types of specific binding—not just a bait-prey interaction or antibody-epitope interaction. In the depicted example, an agent "B" binds to the phosphorylated residue on "A." The detection reagent includes a FRET fluorophore coupled to anti-B antibody.

As was discussed above, certain aspects of the invention rely on the fact that a dye (fluorophore) with a high intrinsic anisotropy that functions as an acceptor in a FRET pair has significantly lower anisotropy than it has when it is not interacting in a FRET pair. A dye, also with a high intrinsic anisotropy, that functions as a donor in a FRET pair, however, has essentially the same anisotropy when it is a donor in a FRET pair and when it is not interacting as a donor in a FRET pair.

A fluorophore with a "high" intrinsic anisotropy may be understood to be a fluorescent species that interacts with linearly polarized excitation light by producing strongly polarized emission light. Quantitatively, the light emitted from a fluorophore with high intrinsic anisotropy will have a calculated anisotropy (using the expression in the Background section of this document) of at least about 0.3, more preferably at least about 0.4, when stimulated with light at the fluorophore's excitation frequency.

An inventive analysis method and system will now be described by way of example of an embodiment that uses the detection system as described above in conjunction with optically encoded beads and/or live cells. It should however be realized that the invention is not limited to beads and live cells, but any type of objects or combinations of objects suitable for FRET analysis can be used. Such examples of objects or combinations thereof include microbeads, spots, spot on spot, spot on a slide combined with a bead, samples or objects confined in capillary tubes or microfluidic channels, and so on. The central idea is to simultaneously measure anisotropy for two different wavelength regions for a sample confined in a well-defined target region, and to use one of the measured anisotropies as an internal reference for detecting and/or quantifying a change of the other measured anisotropy for the sample in the target region, thereby allowing for detection of the presence, absence and/or quantity of FRET in the target region. While the cases described herein use the donor fluorescence as a reference, other sources with known anisotropy can also be used as a reference, including other non-FRET fluorescent molecules present in the assay system or even scattered light signals from an excitation source. In another case, homo-FRET between molecules with high intrinsic anisotropy can be measured by observing the decrease in anisotropy upon FRET. In the case of homo-FRET, where the donor and acceptor have the same emission frequency, a separate reference emission with a known anisotropy and present in the sample can be used as an internal reference to improve quantitation. As the skilled person realizes, these techniques can be advantageously combined with the above-mentioned array based assays. In each case, a feature such as a homo-FRET pair, a scattering center, etc., that produces signal for the internal standard will be co-localized with the assay binding pair.

An experimental example will now be described with reference to FIG. 7, which shows a set of calibration beads of 30 micrometers in diameter to which fluorescent proteins were attached. The fluorescent proteins were excited with laser light of a wavelength of 440 nanometers (that is, within the range of fluorescence absorption for a CFP donor employed in this example), and the fluorescence from the beads was collected using the apparatus of FIG. 1. Bead set A was tagged with CFP and shows a broad fluorescence across both the blue and yellow channels. Bead set B was tagged with a YFP fluorophore and shows fluorescence only in the yellow channel, as expected. Bead set C was tagged with a FRET pair (CFP-YFP) and shows enhanced fluorescence in the yellow channel and reduced fluorescence in the blue channel, resulting from energy transfer from donor to acceptor. Finally, bead set D is a mixture of bead sets A, B, and C, and shows fluorescence in both the blue and yellow channels.

Figure 7:
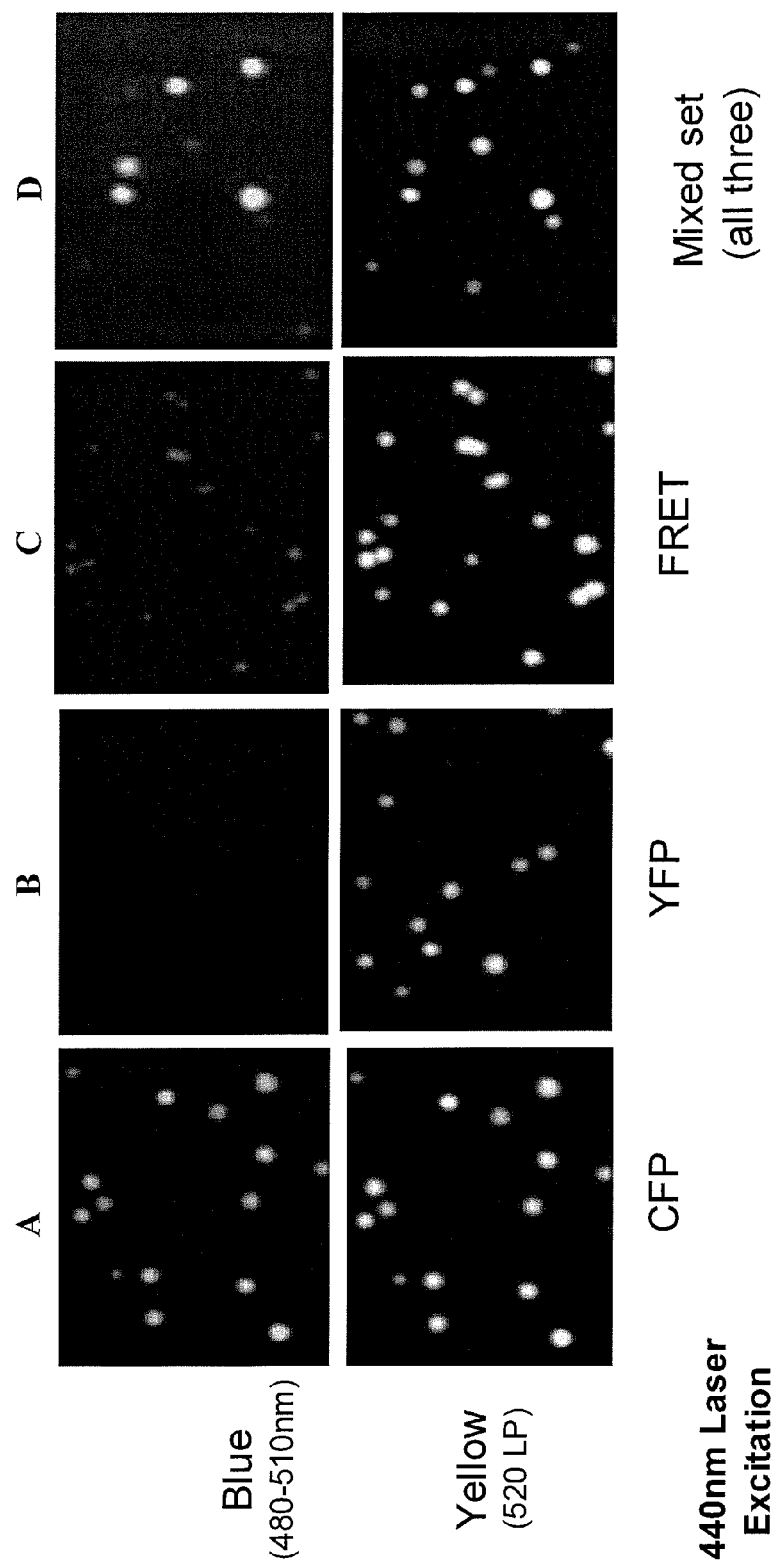
FIG. 7 shows intensity signals obtained in a blue and a yellow channel from various sets of FRET calibration beads.
Figure 8:
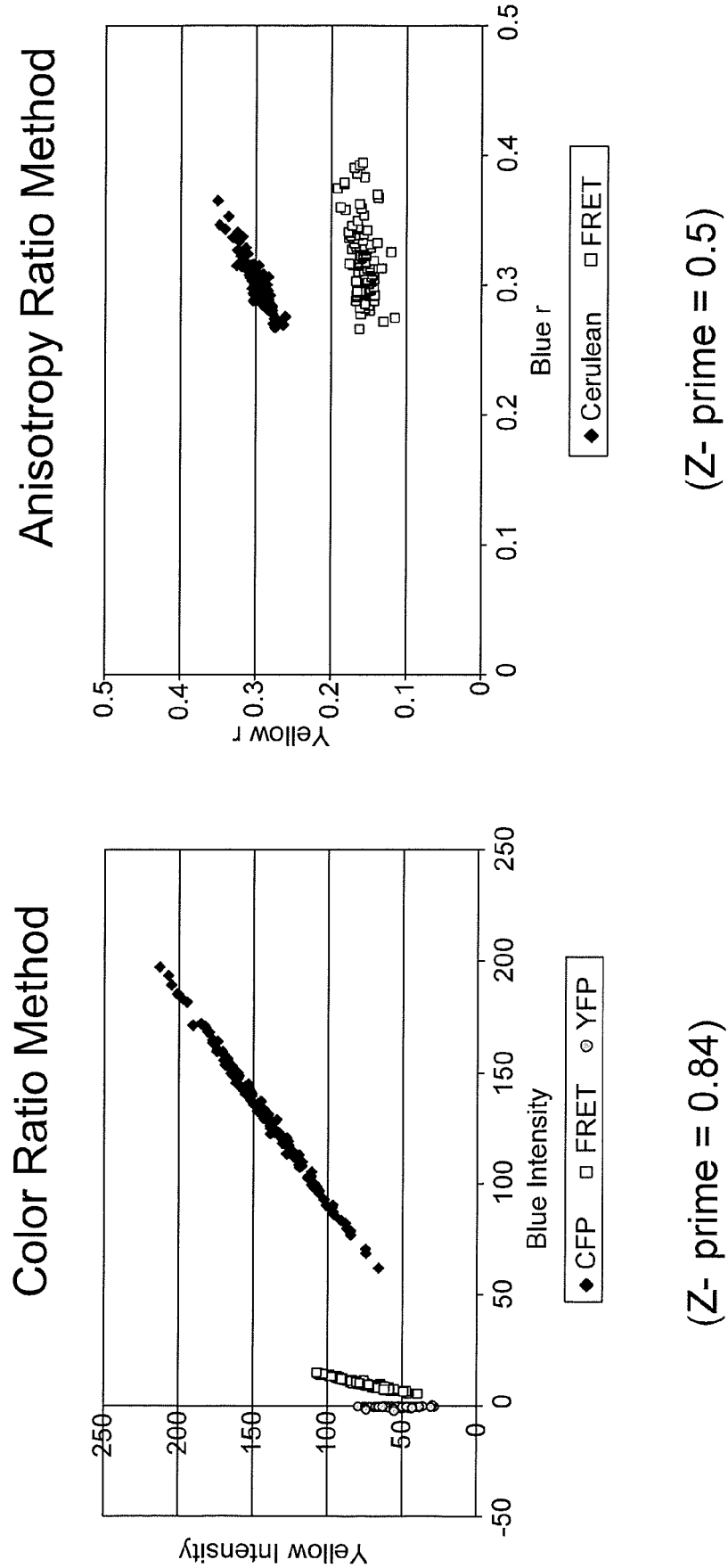
FIG. 8 shows intensity and anisotropy scatter plots for the calibration beads of FIG. 7.

FIG. 8 shows intensity and anisotropy scatter plots for the calibration beads of FIG. 7. As can seen be on the left hand graph of FIG. 8, in the color ratio plot where the measured blue intensity is plotted against the measured yellow intensity, it is easy to separate the CFP bead set from the FRET bead set. The right hand graph of FIG. 8 shows a corresponding plot for the anisotropy for the blue fluorescence and the yellow fluorescence. As can be seen in the anisotropy plot, the CFP bead set is clearly distinguishable from the FRET bead set, which confirms that anisotropy is a useful characteristic for measuring FRET occurrence. Furthermore, what can also be seen from the anisotropy plot of FIG. 8 is that while the anisotropy for the yellow fluorescence changes between the CFP bead set and the FRET bead set, the anisotropy of the blue fluorescence remains the same in both cases. Expressed differently, the CFP and FRET anisotropy scatter plots span basically the same range in the horizontal direction (blue anisotropy), but different ranges in the vertical direction (yellow anisotropy) of the diagram. Thus, the blue anisotropy can be used as an internal reference for measuring a change in the yellow anisotropy. Since the above described apparatus allows the two anisotropies to be measured simultaneously, any local unknowns and calibration factors that are common between the yellow and the blue signal are taken into account, thereby resulting in an improved method for measuring FRET interaction.

Figure 9:
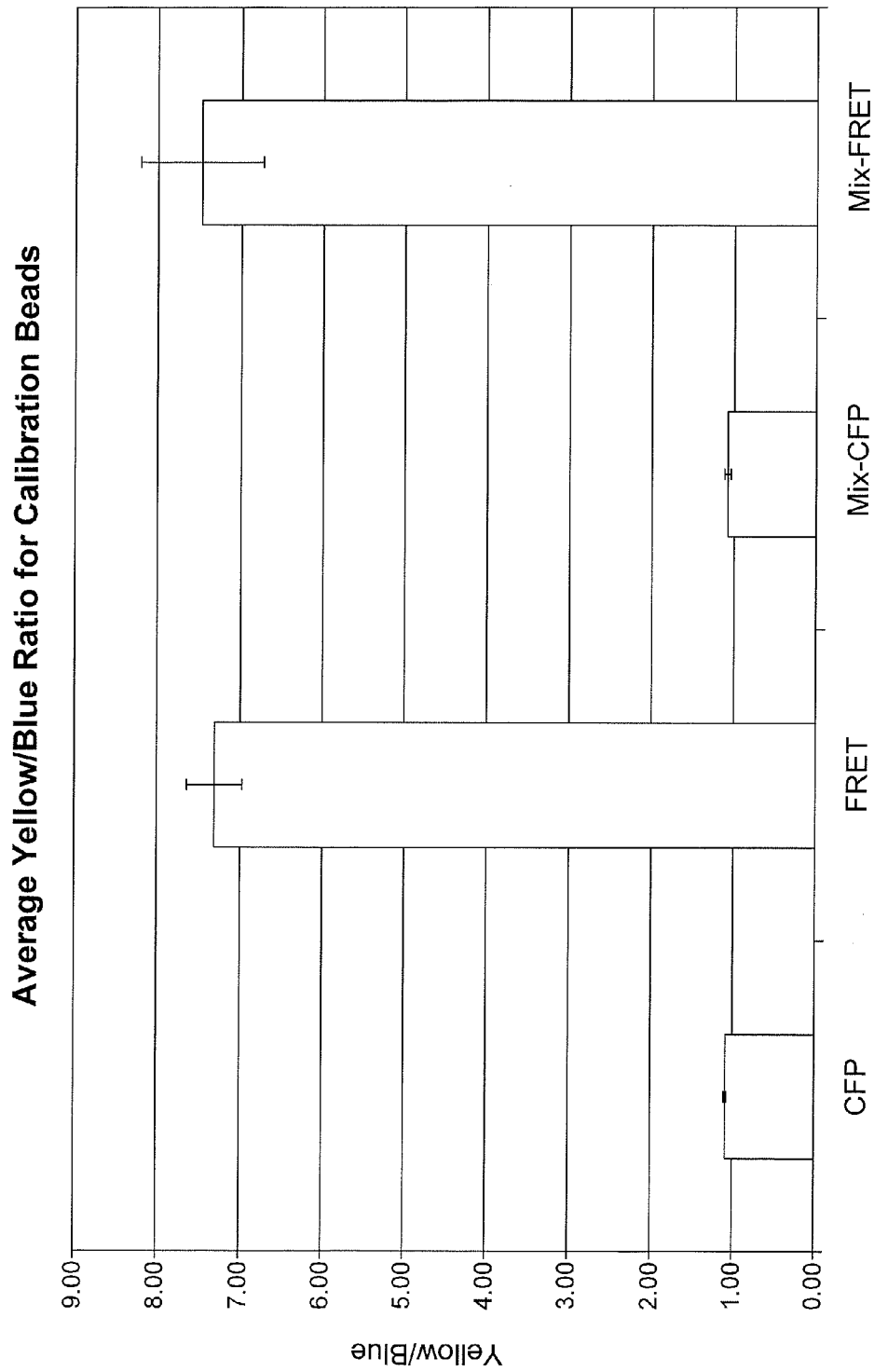
FIG. 9 shows a bar diagram illustrating the average yellow/blue intensity ratios for the calibration beads of FIG. 7.
Figure 10:
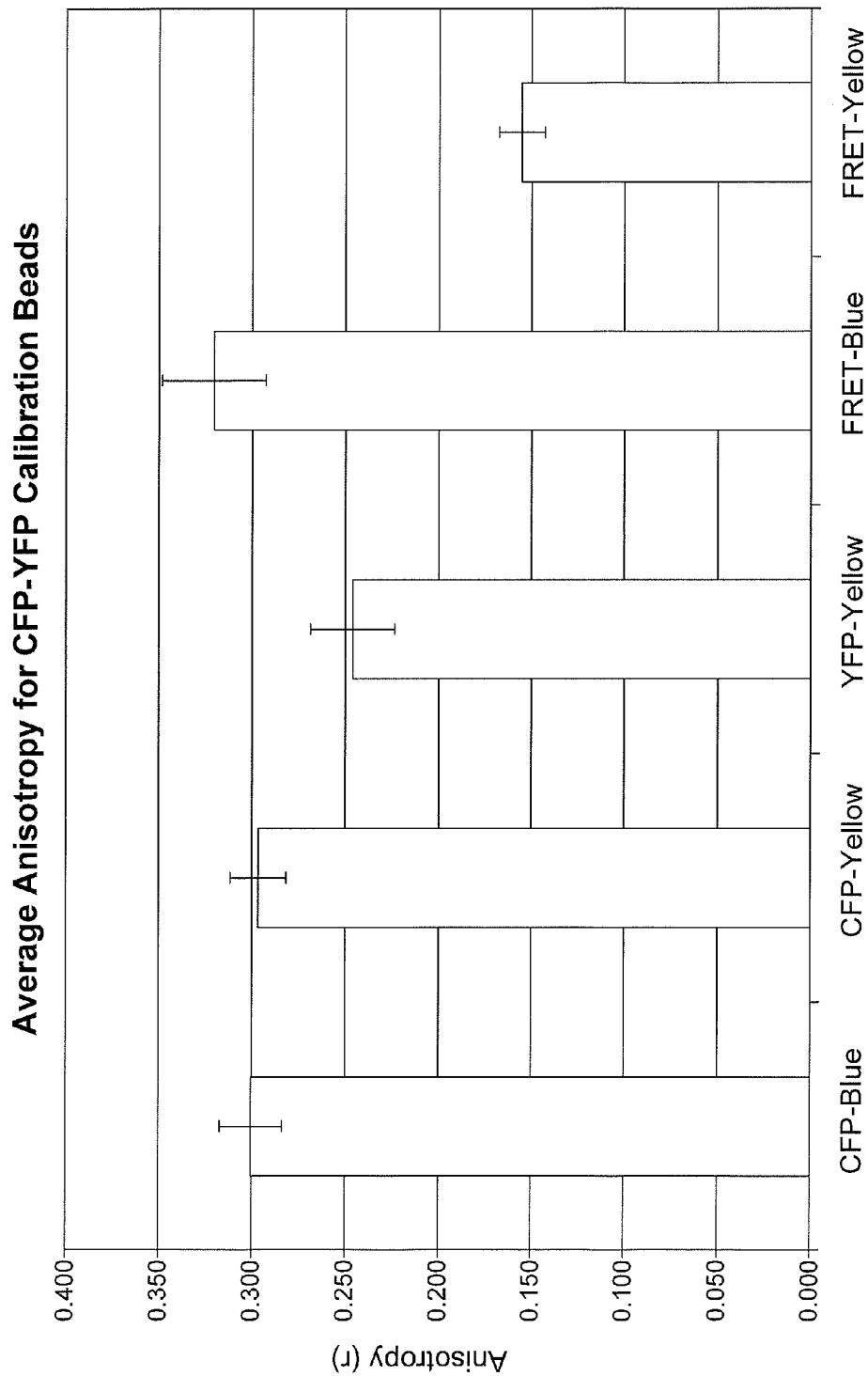
FIG. 10 shows a bar diagram illustrating the average anisotropy for CFP/YFP calibration beads of FIG. 7.

FIGS. 9 and 10 show bar diagrams corresponding to the intensity and anisotropy scatter plots, respectively, in FIG. 8. In FIG. 9, the two bars on the left hand side show the ratios of the measured yellow and blue intensities ((yellow intensity)/(blue intensity)) for the CFP and FRET bead sets of FIG. 7. The two bars on the right hand side show that the intensity ratios stay essentially the same also when the bead sets are placed together as a mixture in the same well, that is, "mixed." Furthermore, it is clear from FIG. 9 that in both cases, the occurrence of FRET interaction is easily distinguishable from non-FRET fluorescence by CFP. In FIG. 10 the average anisotropy for CFP and YFP for the calibration beads are shown. The two left hand bars show that CFP anisotropy in both the blue and yellow channels is around 0.3, which is relatively high in comparison to other samples provided in this experiment. The YFP anisotropy in the yellow channel is a little bit lower, which is likely due to YFP's lower "intrinsic anisotropy," that is, the mechanism by which the YFP is excited and fluoresces may cause the YFP to have an initially lower anisotropy.

As can be seen in the two right-most bars, the FRET signal shows significantly increased separation of blue anisotropy and yellow anisotropy. In fact, the blue anisotropy has increased in comparison to the non-FRET example, while FRET-yellow anisotropy has decreased. The increase for the FRET-blue anisotropy likely stems from a decrease in fluorescence lifetime of the CFP because of FRET, resulting in slightly less opportunity for the blue donor fluorophore to undergo changes that would introduce randomness into the polarization state of its emitted frequency. In other words, the emission from the donor fluorophore is limited by transmission of some energy to the acceptor fluorophore that would otherwise go to emission of fluorescence radiation, and the remaining energy that is emitted by the donor has a high anisotropy. The FRET-yellow is a combination of the direct excitation of the CFP (some emission by CFP at the yellow end of spectrum), direct excitation of the YFP (by the radiation used to stimulate CFP), and a YFP emission resulting from FRET. The anisotropy will vary for each of these components, so what the rightmost bar represents is a weighted average of the anisotropy in each of these factors. The first two factors should result in relatively high anisotropy. Even so, the FRET-yellow average anisotropy is significantly lower than the other average anisotropies of FIG. 10, and is thus a good indicator for FRET interaction.

Figure 11:
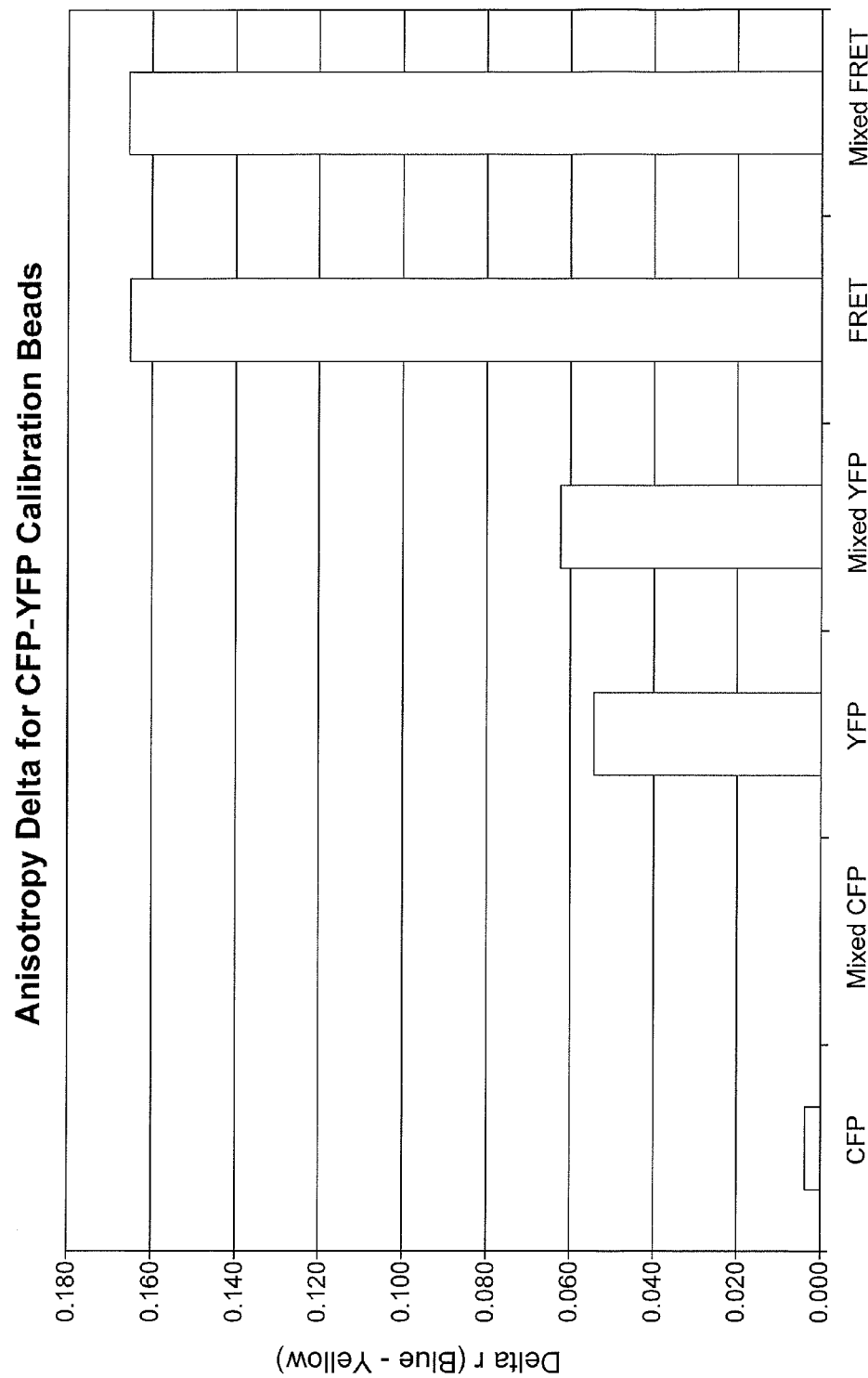
FIG. 11 shows a bar diagram showing the anisotropy difference for the CFP/YFP calibration beads of FIG. 7.

FIG. 11 is a bar diagram showing the differences in blue and yellow anisotropy for CFP beads, YFP beads, and FRET beads in separate and mixed sets, respectively. As can be seen from FIG. 11, the differences in yellow and blue anisotropy are essentially the same whether the beads are studied one type at a time, or as a set of mixed beads. It can also be seen from FIG. 11 that there is a much larger difference in the blue and yellow anisotropy for FRET interactions than CFP and YFP, respectively, and thus that FRET interaction can be easily separated from the CFP and YFP, respectively.

Figure 12:
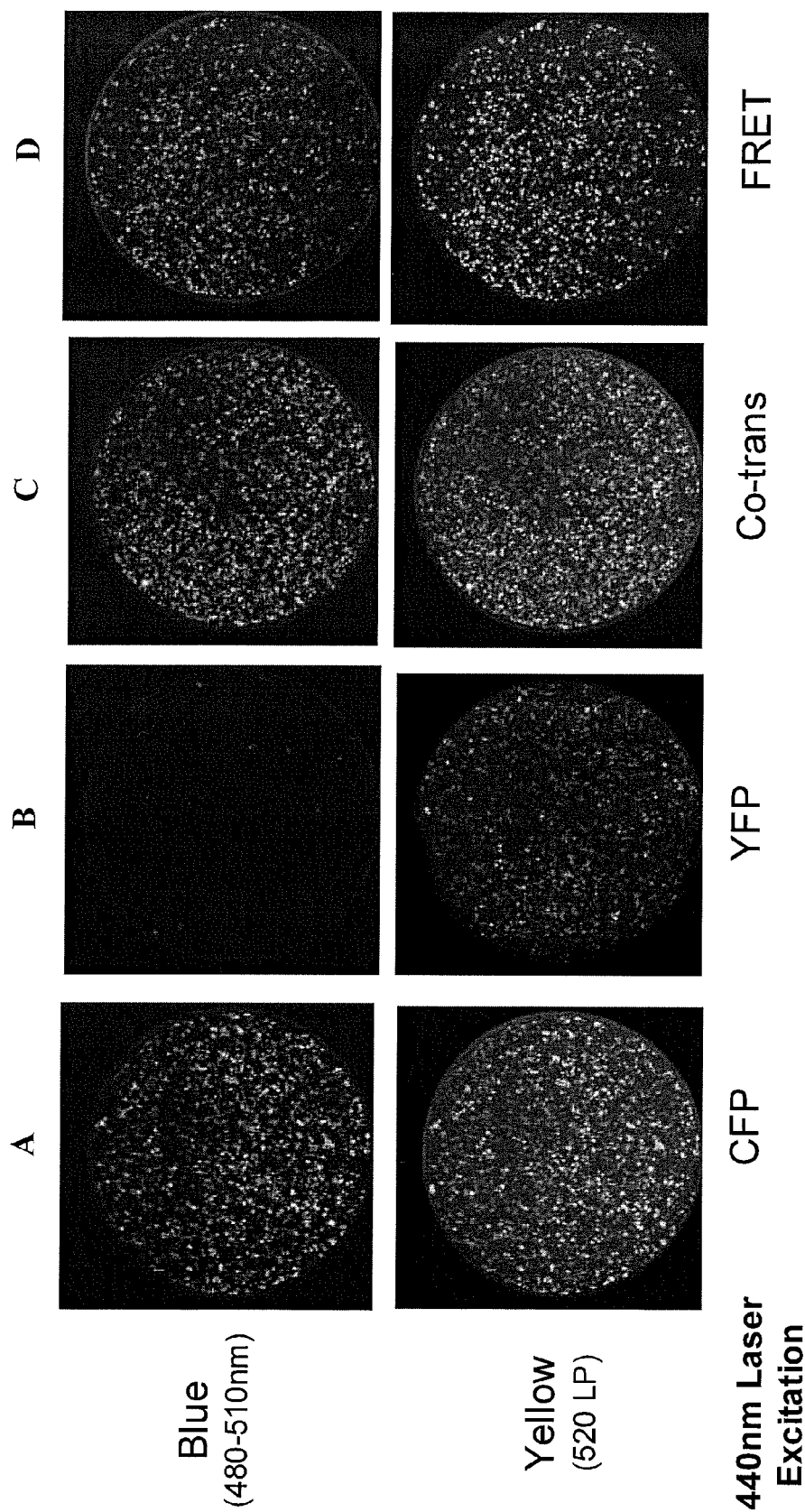
FIG. 12 shows intensity signals obtained in a blue and a yellow channel from various sets of transfected live cells.

Next, an example will be presented showing how FRET can be identified for CFP/YFP transfected live cells. FIG. 12 shows images of Cos-7 cells that were transfected with mCer-N3, mVenus-C1 and SCAT3.1 (a CFP/YFP FRET sensor for caspase-3 activation). Caspase activity may be used as an indicator of apoptosis in some populations of cells. In this example, the transfections were made in a 96-well glass bottom plate, and the cells were transfected for 24 hours. The cells were then irradiated with laser light of a wavelength of 440 nanometers (a fluorescence stimulation frequency for CFP), and the fluorescent light from the cells was collected using an apparatus having some features of the system described in FIG. 1. As shown in the figure, cells A were transfected with CFP (Cerulean), cells B were transfected with YFP (Venus), cells C were co-transfected with CFP and YFP, that is, the CFP and YFP were added separately and not as a FRET pair, and finally cells D were transfected with two proteins that interact such that they are located within 40 Angstroms distance from each other, allowing for FRET interaction to occur. FRET technology can provide significant information about the dynamics and pattern of endogenous caspase activation in vivo. Recombinant caspase substrates composed of enhanced cyan fluorescence protein (ECFP) may be used as the FRET donor and enhanced yellow fluorescence protein (EYFP) as the FRET acceptor, linked by peptides containing the caspase-3 cleavage sequence (DEVD). The development of such indicators enables researchers to monitor caspase activation at the single-cell level in real time. As can be seen in FIG. 12, the fluorescence patterns for the various cell groups are similar to the ones for the calibration beads discussed above with respect to FIG. 7. However in the case of the SCAT sensor, the FRET disappears once the Caspase is activated, thus sensing the apoptosis event. The FRET interaction and signal expressed as a SCAT3.1 sensor is shown here prior to caspase-3 activation and cleavage.

Figure 13:
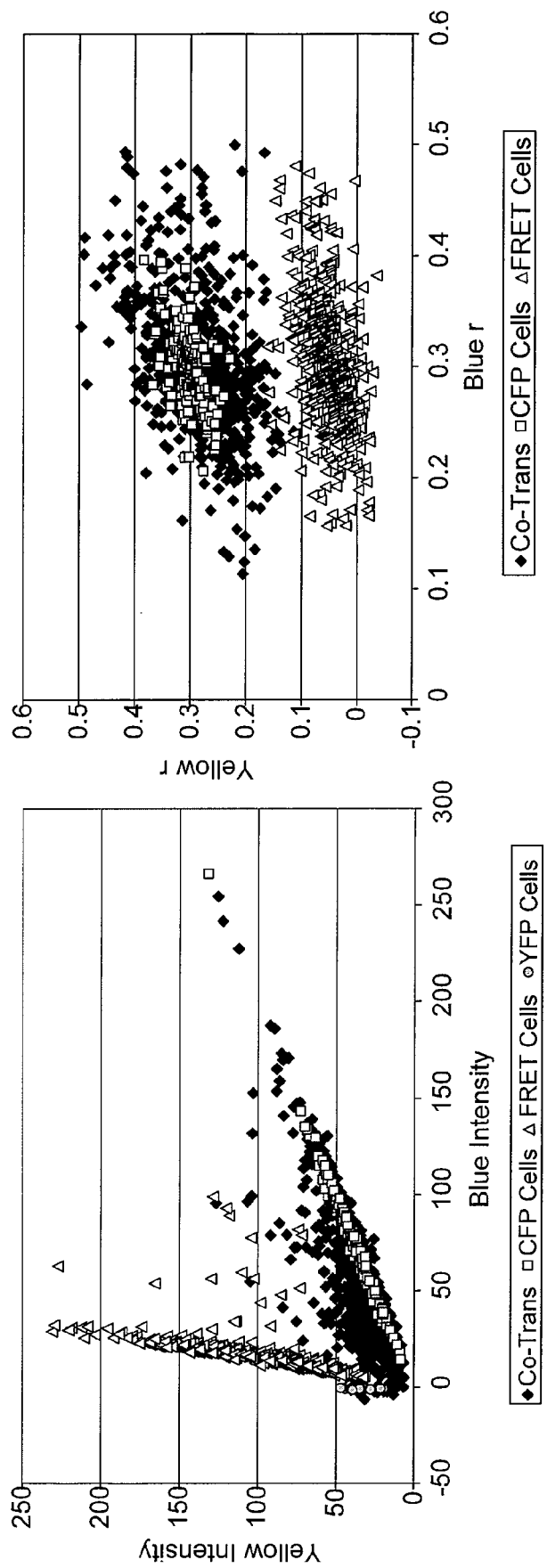
FIG. 13 shows intensity and anisotropy scatter plots for the cells of FIG. 12.

FIG. 13 shows intensity and anisotropy scatter plots for the live cells of FIG. 12. As can seen in FIG. 13, the plots are very similar to the plots that were obtained for the calibration beads in FIG. 8. Especially, as can be seen in the anisotropy scatter plot on the right hand side of FIG. 13, the FRET anisotropy can be easily separated both from the co-transfected cells and from the CFP cells.

Figure 14:
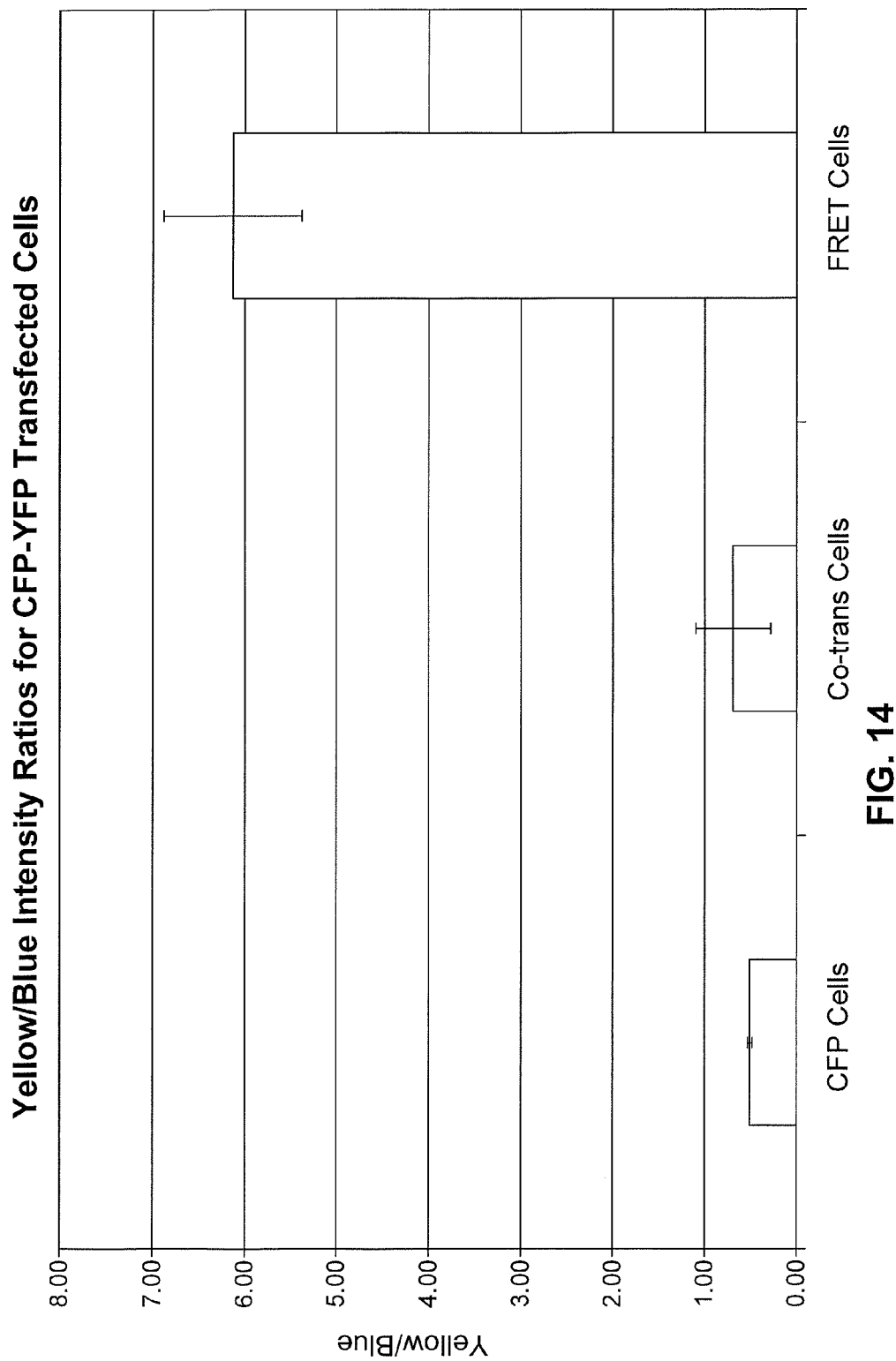
FIG. 14 shows a bar diagram illustrating the average yellow/blue intensity ratios for the cells of FIG. 12.

FIG. 14 shows bar diagrams corresponding to the intensity plots, respectively, in FIG. 13. As can be seen in FIG. 10, FRET cells are easily distinguishable from CFP and co-transfected cells, respectively.

Figure 15:
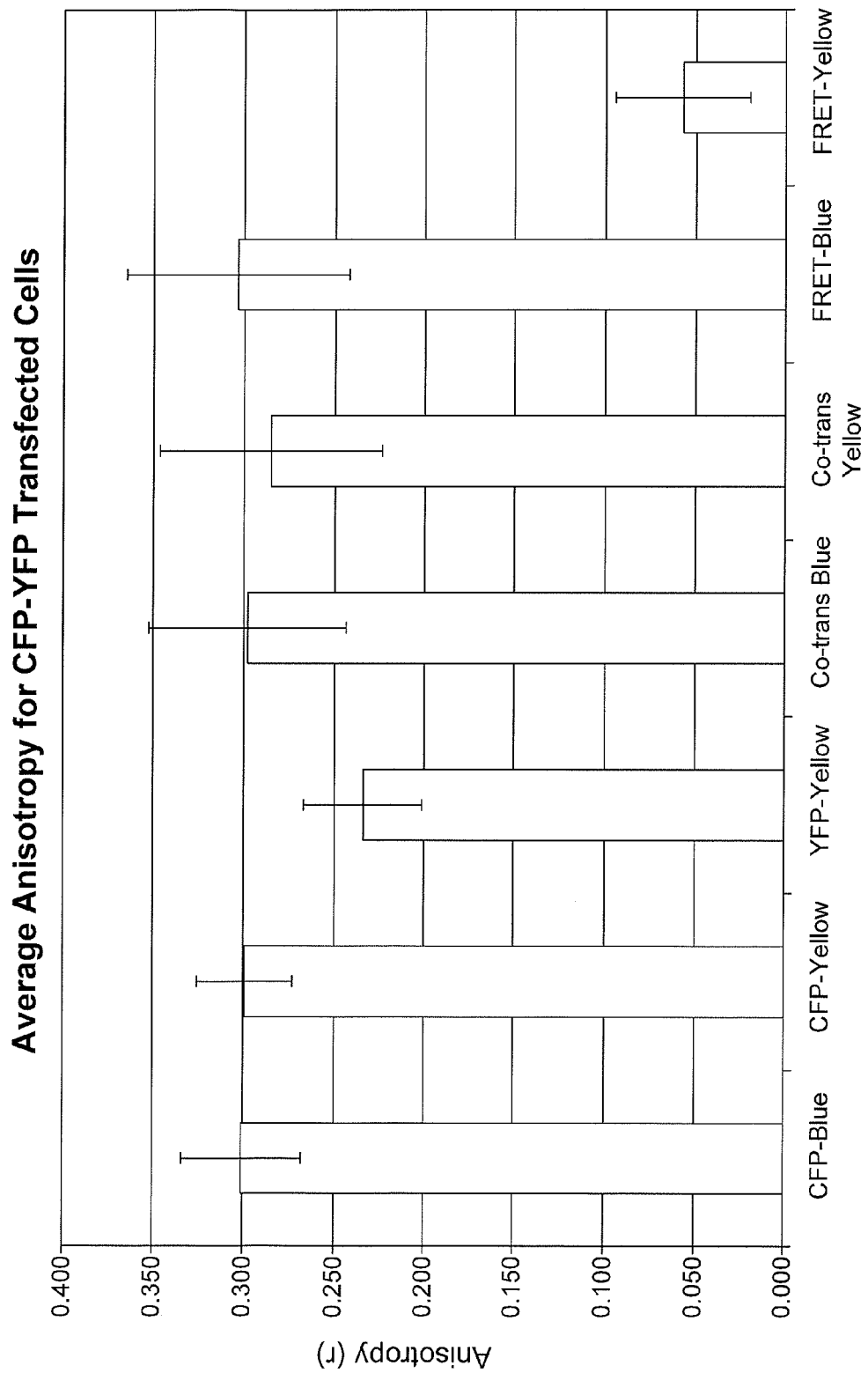
FIG. 15 shows a bar diagram illustrating the average anisotropy for CFP/YFP cells of FIG. 12.

FIG. 15 shows the average anisotropy for CFP/YFP transfected cells. Again, the results are similar to what was obtained with the calibration beads and shown in FIG. 10. The FRET-yellow average anisotropy is significantly lower than the other average anisotropies of FIG. 11, and is thus a good indicator for FRET interaction.

Figure 16:
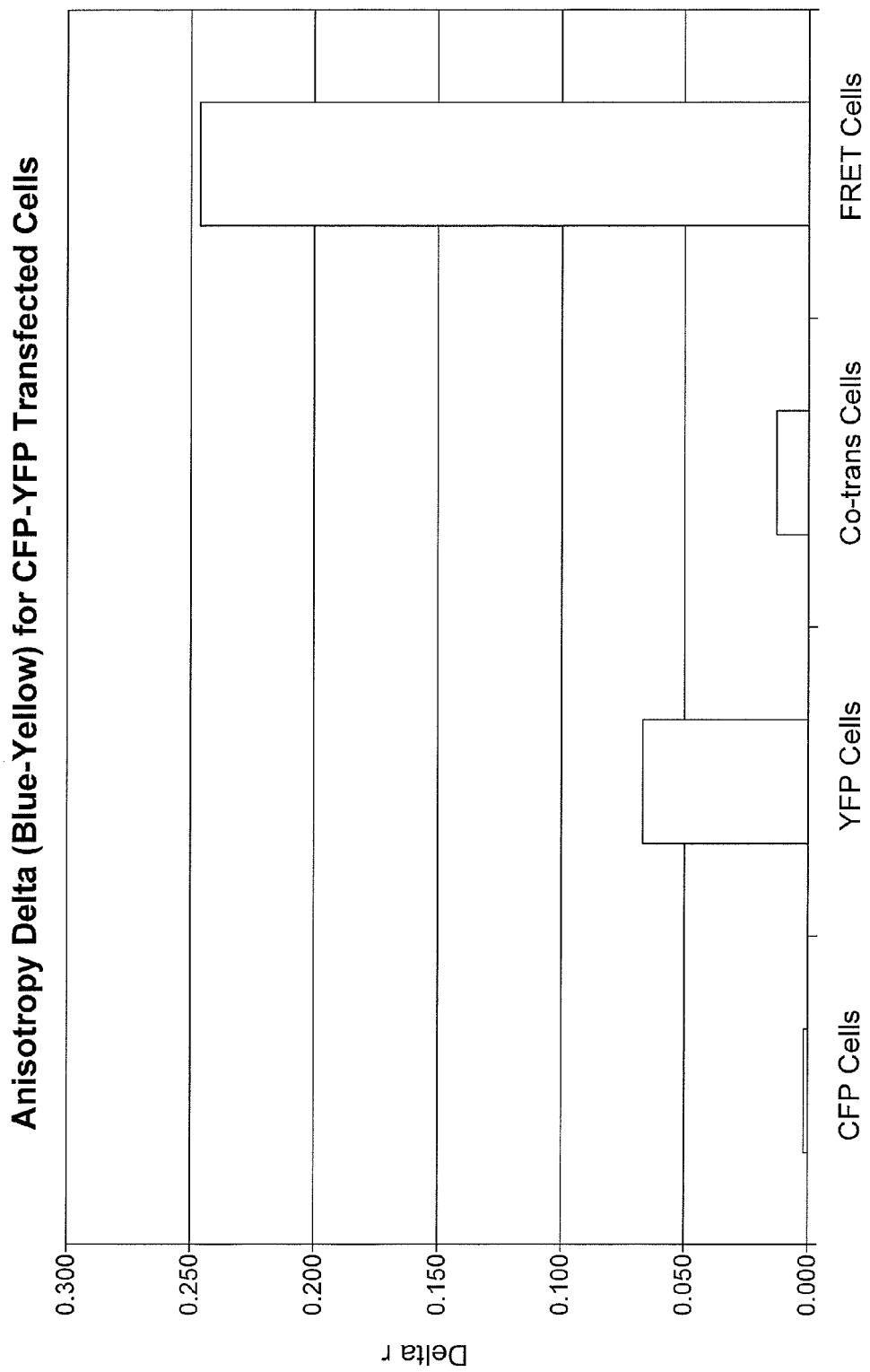
FIG. 16 shows a bar diagram showing the anisotropy difference for the CFP/YFP transfected cells of FIG. 12.

FIG. 16 is a bar diagram showing the differences in blue and yellow anisotropy for CFP cells, YFP cells, co-transfected cells, and FRET cells. As can be seen from FIG. 16, there is a much larger difference in the blue and yellow anisotropy for FRET cells than for CFP cells, YFP cells, and co-transfected cells, respectively, and thus the FRET cells can be easily distinguished from the other cells.

Figure 17:
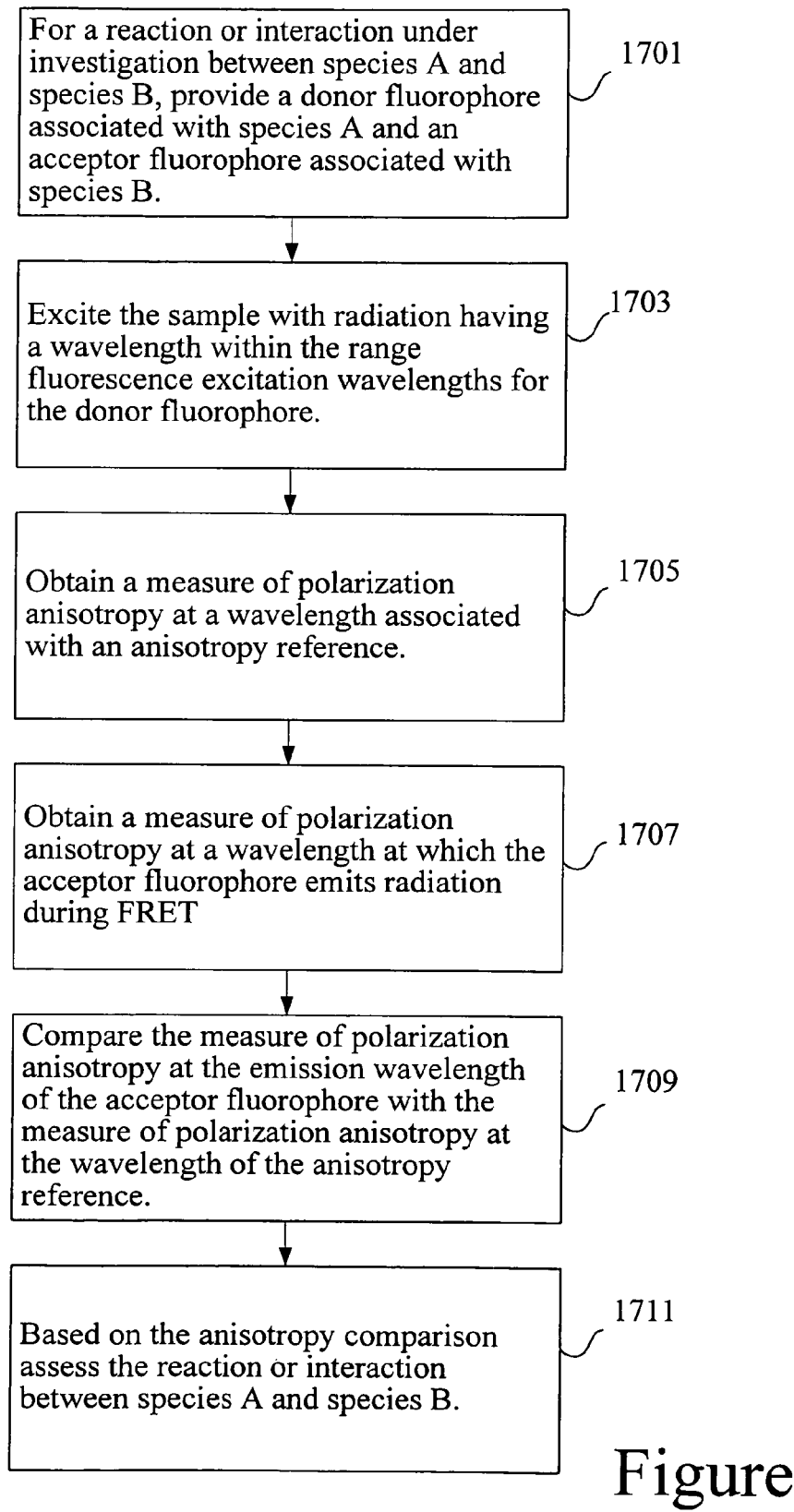
FIG. 17 is a flow chart depicting operations that may be relevant in certain embodiments employing polarization anisotropy references.

A summary of certain process embodiments of the invention will now be provided. FIG. 17 presents a flow chart depicting some of the operations that may be employed in some embodiments. While the flow chart is presented as a sequential series of operations, the invention is not limited to the order presented. Further, as explained, some of the operations may be conducted simultaneously. Other operations may be performed in an order reversed from that depicted.

The process depicted in FIG. 17 assumes that an assay is performed for an interaction between a species A and B. Species A and species B are sometimes referred to herein as first and second chemical entities. These terms are intended to broadly cover various molecules, molecular fragments, complexes, assemblies of molecules, molecular superstructures, cell components including organelles, and the like. Many biomolecules may serve as chemical entities. Examples include nucleic acids, proteins and peptides, lipids, carbohydrates, and combinations thereof. As indicated, methods and apparatus of the present invention may measure changes in interaction between the first and second chemical entities. These changes may be caused by binding between the entities, cleavage of structure including the entities, change in the conformation of one or both entities (e.g., folding of a protein), steric hindrance of one or both entities, chemical modification of an entity (e.g., phosphorylation), which may affect binding, conformation, etc., oligomerization, and the like.

As shown in top-most block of FIG. 17, operation 1701, components that may be provided in a typical sample include a donor fluorophore associated with species A and an acceptor fluorophore associated with species B. Typically, though not necessarily, the components of the sample are allowed to remain in contact (as by contact with a single solution) for a period of time. In other embodiments, where time-resolved tracking of the interaction is desired, the sample may be probed for FRET immediately. In FIG. 17, the probing is depicted in a block 1703, where the system in which the assay is conducted provides excitation radiation having a wavelength within the range fluorescence excitation wavelengths for the donor fluorophore.

At some point in the process, the system obtains a measure of polarization anisotropy at a wavelength associated with an anisotropy reference. See block 1705. This may entail providing excitation radiation at a wavelength distinct from that applied in operation 1703. However, for many embodiments, a single excitation source—one at the excitation frequency of the donor—will be sufficient. As shown in block 1707, the process also involves obtaining a measure of polarization anisotropy at a wavelength at which the acceptor fluorophore emits radiation during FRET. With this information, the system may compare the measure of anisotropy at the emission wavelength of the acceptor with the measure of anisotropy at the wavelength of the anisotropy reference. See block 1709. Based on this anisotropy comparison, the process assesses the reaction or interaction between species A and species B. See block 1711.

This interaction or reaction mentioned in block 1701 is typically conducted in a designated sample region such as a small, sometimes confined area where species A, species B, the donor fluorophore and the acceptor fluorophore are mixed or otherwise allowed to come into intimate contact with one another. Typically, though not necessarily, the sample regions are wells or spot regions on a multi-well plate, or regions in a flow channel. Other examples include (a) in situ analysis of a tissue or organ sample, a blood flow, etc., (b) flat rotating substrates as described in U.S. patent application Ser. No. 11/055,244, filed Feb. 9, 2005 (incorporated herein by reference for all purposes), (c) in situ analysis of cells or compartments within cells such as the nucleus or cytoplasm, and (d) in situ analysis of aggregates of cells, such as cell colonies, where distinct regions or specific aggregates may be undergoing specific interactions causing a FRET signal.

As indicated above, the donor and acceptor fluorophores should be capable of forming a FRET pair. Many suitable fluorophore pairs are familiar to those of skilled in the art. In addition to the fluorescent protein pairs exemplified above, other fluorescent entities suitable for participating in FRET pairs include fluorescein, rhodamines, the Bodipy family of dyes (available from Invitrogen Corporation of Carlsbad, Calif.), ethidium bromide, fluorescent coumarins, cyanine dyes, etc. Various fluorescent proteins (typically provided as chimeric fusion proteins in vivo) may be employed. These include he red fluorescent protein cloned from Discosoma coral (DsRed or drFP583), green fluorescent protein (GFP), blue, cyan, and yellow variants of GFP, cyan fluorescent protein, and yellow fluorescent protein, to name a few.

Initially, when the components of the assay are brought together, species A and B may be either physically separated or linked. Separated species may be binding or reacting pairs that are brought into contact in order to assess whether the binding or reacting takes place in the assay sample. In such cases, the assay may begin with relatively high polarization anisotropy in the signal from the acceptor's emission frequency. But when or if the reaction takes place, there will be a detectable decrease in polarization anisotropy from the acceptor emission. In another case, when species A and B are initially linked and then exposed to conditions which might potentially cleave them or otherwise cause them to become further separated from one another, the reaction or interaction under investigation will result in a detectable increase in polarization anisotropy in signal collected at the acceptor's emission wavelength.

Regarding operation 1703, the excitation source for the assays described herein is typically linearly polarized or otherwise strongly polarized. It is provided in a narrow frequency band at the excitation frequency of the donor fluorophore, although this is not always necessary, particularly if the excitation frequency of the acceptor fluorophore, as well as the emission frequencies of the donor and acceptor fluorophores, is well removed from the excitation frequency of the acceptor. The intensity of the excitation radiation is chosen as appropriate for the assay under consideration. Typically, one wishes to provide a sufficiently high intensity to produce strong FRET signals, but not so high that it interferes with the species undergoing reaction. For many in vitro assays, the intensity range of the source (as it interacts with the sample—accounting for losses caused by the optics) will be between about $1 \times 10^3$ and $2 \times 10^5$ Watts/cm$^2$. More typically, the range will between about $2 \times 10^3$ and $2 \times 10^4$ Watts/cm$^2$.

Regarding operation 1705, a reference is provided for calibration or comparison of the polarization anisotropy signal from the sample. As mentioned, the local conditions of the assay other than FRET interactions may impact anisotropy independently. As a consequence, it is sometimes preferable to measure a relative, rather than an absolute value of anisotropy. Obtaining the polarization anisotropy from the reference may be accomplished as describe elsewhere herein, namely by determining the degree to which the reference signal is polarized. Typically this is obtained by measuring signal at two orthogonal polarization angles, one parallel to the polarization direction provided by the excitation source and the other perpendicular to that direction. Significant differences in the intensity taken in the two directions indicates high anisotropy, whereas more equal values of intensity taken across the two directions indicates isotropy. Again, the anisotropy of the reference is taken for the purpose of calibrating the anisotropy measured for the sample's acceptor fluorophore emission.

As mentioned, a reference may be an internal reference or an external reference. An internal reference signal is typically obtained from the anisotropy of the donor fluorophore's emission signal. An external reference is taken from a source other than the donor's fluorescent emission. As mentioned, one example is emission from a reference, non-donor, non-acceptor fluorophore within the sample. Such reference may be immobilized on the sample containment vessel, provided on a bead within the sample, provided in solution, etc. Another example of an external reference is radiation from the excitation source as measured in the sample; for example scattered light collected from the sample.

Regarding operation 1707, the polarization anisotropy of the acceptor fluorophore's emission frequency is measured in the same way as the polarization anisotropy of the reference, but at a different wavelength. As explained above, depending on whether the interaction under investigation brings species A and B into closer proximity or separates them, a decrease or increase in polarization anisotropy at the acceptor's emission frequency will be a signature for the interaction.

Regarding operations 1709 and 1711, the comparison and assessment will typically take place using a computer, circuitry, or specially constructed logic. A threshold level of difference in anisotropy between the sample and the reference may be used to indicate that the reaction or interaction is taking place. Alternatively or in addition, a quantitative value of the difference in anisotropy may be used to indicate the extent to which the reaction or interaction is taking place. In certain embodiments, the relative anisotropy value provides an indication of the concentration or potency of species A or species B.

Figure 18:
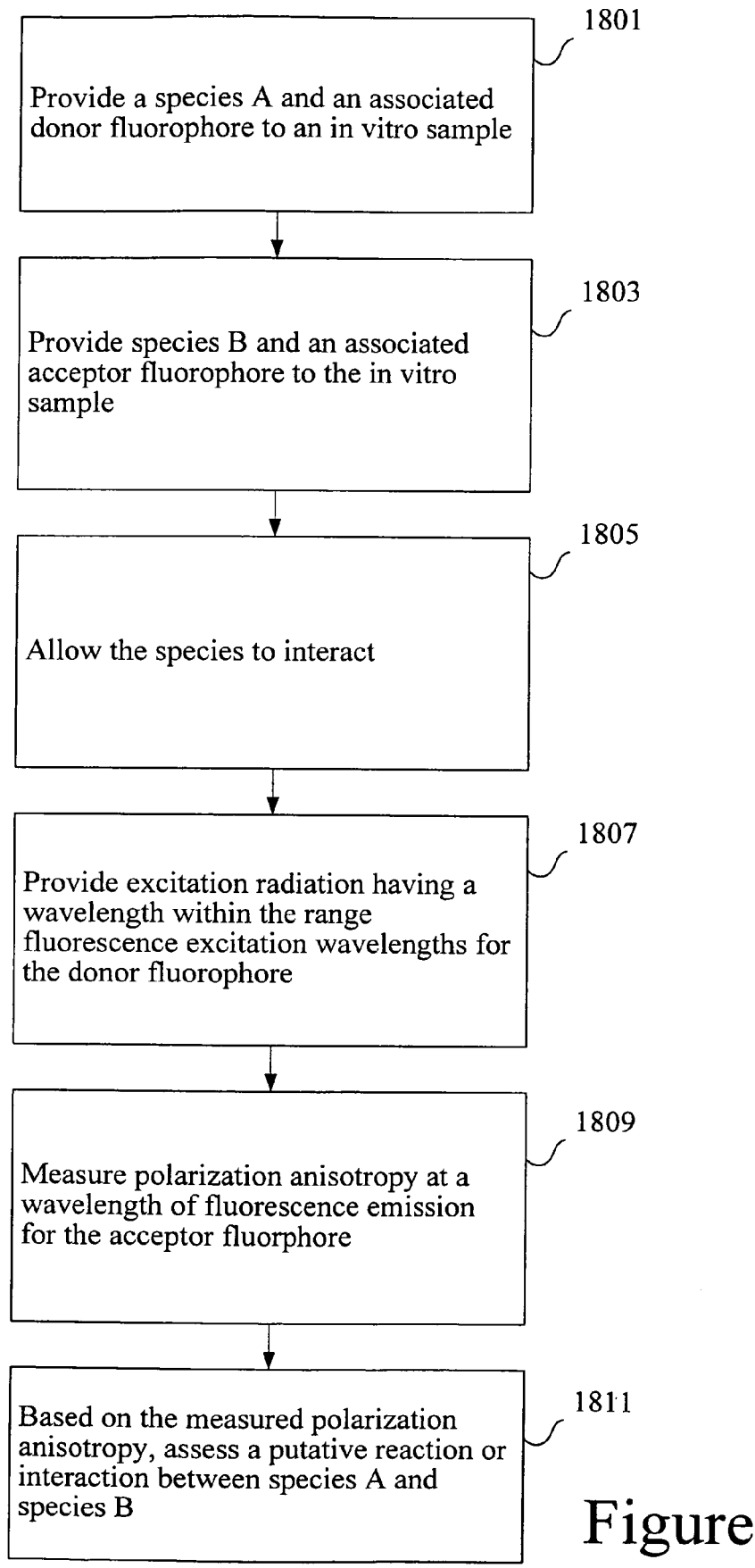
FIG. 18 is a flow chart depicting operations that may be relevant in certain embodiments employing polarization anisotropy in in vitro assays.

FIG. 18 presents another flow chart depicting a general sequence of operations for conducting in vitro assays. As depicted in an initial block 1801, a species A and an associated donor fluorophore are provided to an in vitro sample. As indicated in a block 1803, a species B and an associated acceptor fluorophore are also provided to the in vitro sample. Note that together operations 1801 and 1803 may simply comprise mixing two solutions—one containing species A and its fluorophore and another containing species B and its fluorophore—to form the assay sample. In certain embodiments, however, it will be appropriate to add one or both of the fluorophores as separate components. Note also that if species A and B together form a linked structure such as a substrate for caspase-3 or other active biomolecule, then operations 1801 and 1803 are performed as a single operation. Regardless of how they are performed, operations 1801 and 1803 together represent preparing the assay sample. In high throughput systems, many different assay samples are created and probed in rapid succession.

In some embodiments, prior to probing FRET interactions, the species and fluorophores are allowed to interact as necessary, sometimes for a defined period of time or after exposure to a particular stimulus such as elevated temperature, low oxygen, etc. See block 1805. After the sample under investigation is prepared, it is probed by exposing it to excitation radiation having a wavelength within the range fluorescence excitation wavelengths for the donor fluorophore. See block 1807.

After exposing the assay sample to excitation radiation, the system measures polarization anisotropy at a wavelength of fluorescence emission for the acceptor fluorophore. See block 1809. As explained above, this information is used to determine whether FRET is occurring. Based on the measured polarization anisotropy, the process assesses whether a putative reaction or interaction between species A and species B has taken place. See block 1811. If it is determined that the reaction took place, some embodiments of the invention optionally determine the degree to which it took place.

Certain embodiments of the invention pertain to a device, system or apparatus for performing the aforementioned operations. The system may be specially constructed for the required purposes, or it may be a general-purpose optical instrument, selectively activated or configured by, for example, a computer program stored in the computer. The processes presented above are not inherently related to any particular optical instrument or computing apparatus.

A number of implementations of the invention have been described. Nevertheless, it will be understood that various modifications may be made without departing from the spirit and scope of the invention. For example, the above description has been focused on spot array and live cell formats for the assays. The invention is of course not limited in this manner. As another example, the solid substrate may comprise beads. In the spot array format, a wide variety of capture area sizes may be employed depending on the application. The spot density will also vary depending on the application. In a specific example, the substrate comprises wells and these sized as appropriate for the application; e.g., spot sizes of approximately 50 nl or smaller. The pattern of wells or spots may encode or provide particular information such as bar code information. In a specific application, the substrates are designed to provide patterns of antibody arrays for core members of signaling pathways. The pattern of spots may contain materials used to generate a reference measurement or control signal for either the assay or the signal readout, or may be simply used as a locating device (fiducial) for the assay spot array. Accordingly, other embodiments are within the scope of the following claims.

What is claimed is:

1. A method for detecting specific binding between a first chemical entity and a second chemical entity, the method comprising:
    immobilizing the first chemical entity in association with a first fluorophore;
    allowing the second chemical entity to bind with the immobilized first chemical entity, wherein the second chemical entity is or becomes coupled to a second fluorophore, which forms a FRET pair with the first fluorophore;
    exposing the bound chemical entities to radiation at an excitation frequency for either the first or the second fluorophore; and
    measuring polarization anisotropy of a FRET fluorescent signal from the bound chemical entities to detect specific binding between the first and second chemical entities, wherein the polarization anisotropy is measured at a first wavelength and a second wavelength.

2. The method of claim 1, further comprising measuring donor emission lifetime of at least one of the first or second fluorophores.

3. The method of claim 1, wherein both the first fluorophore and the second fluorophore have an intrinsic anisotropy of at least about 0.25.

4. The method of claim 1, wherein the polarization anisotropy is measured at a single wavelength.

5. The method of claim 1, wherein at least one of the first and second chemical entities is a biomolecule.

6. The method of claim 5, wherein the biomolecule is a protein.

7. The method of claim 1 wherein the first and second fluorophores are the same (homo-FRET).

8. The method of claim 1, wherein one of the first and second chemical entities comprises a protein and the other of the first and second chemical entities comprises a nucleic acid.

9. The method of claim 1, further comprising performing a defined treatment on at least one of the first and second chemical entities, wherein the specific binding between the first and second chemical entities only occurs when the defined treatment results in at least one of the first and second chemical entities entering a particular state.

10. The method of claim 1, further comprising comparing the anisotropy of the first and second wavelengths to determine whether a FRET interaction is occurring.

11. The method of claim 1, further comprising using the anisotropy at a first wavelength as a reference to determine a change in the anisotropy of the second wavelength.

12. The method of claim 1, wherein the anisotropies of the first and second wavelengths are measured simultaneously.

13. The method of claim 1, wherein the anisotropies of the first and second wavelengths are measured sequentially.

14. The method of claim 1, further comprising measuring a polarization anisotropy of a reference source.

15. The method of claim 14, wherein the reference source is a laser excitation source for one of the fluorophores.

16. The method of claim 14, wherein the reference source is an excitation source other than a laser excitation source for fluorescence.

17. The method of claim 14, further comprising comparing the anisotropy of the first and second wavelengths to the anisotropy of the reference source to determine whether a FRET interaction is occurring.

18. The method of claim 14, further comprising using the anisotropy of the reference source as a reference to determine a change in the anisotropy of the first wavelength or the second wavelength.

19. The method of claim 14, wherein the anisotropies of the first and second wavelengths and the reference source are measured simultaneously.

20. The method of claim 14, wherein the anisotropies of the first and second wavelengths and reference source are measured sequentially.

21. The method of claim 14, wherein the reference source is a spot of a fluorescent dye that has been printed or deposited on a substrate used for measurement.

22. The method of claim 14, wherein the reference source is a fluorescent dye impregnated or incorporated into a substrate or bead material used for measurement.

23. A method for detecting whether a FRET interaction is occurring between a first chemical entity in association with a donor fluorophore and a second chemical entity in association with an acceptor fluorophore, the method comprising:
exposing at least one of the fluorophores to radiation at an excitation wavelength for the donor fluorophore;
measuring a polarization anisotropy of a fluorescent signal at an emission wavelength for the donor fluorophore and at an emission wavelength for the acceptor fluorophore; and
comparing the measured anisotropies to determine whether a FRET interaction is occurring between the first and second chemical entities.

24. The method of claim 23, where both the donor and the acceptor fluorophore has an intrinsic anisotropy of at least about 0.25.

25. The method of claim 23, wherein using the anisotropy at the donor fluorophore's emission wavelength serves as an internal reference to determine or quantify a change in the anisotropy of the acceptor fluorophore's emission wavelength.

26. The method of claim 23, wherein the anisotropies of the donor fluorophore and acceptor fluorophore are measured simultaneously.

27. The method of claim 23, wherein the anisotropies of the first and second wavelengths are measured sequentially.

28. The method of claim 23, wherein a FRET interaction is determined to occur when the measured anisotropy at the emission wavelength of the acceptor fluorophore changes relative to the measured anisotropy at the emission wavelength of the donor fluorophore.

29. The method of claim 23, wherein the first and second chemical entities are included in a target region for FRET analysis, the target region including one or more of microbeads, spots, spot on spot, spot on a slide combined with a bead, samples or objects confined in a capillary tube, samples or objects confined in a microfluidic channel, aggregates or colonies of cells confined in a liquid region such as a well or droplet, and aggregates or colonies of cells immobilized on a surface or surface layer.

30. The method of claim 23, wherein the donor fluorophore is a Cyan Fluorescent Protein and the acceptor fluorophore is a Yellow Fluorescent Protein.

31. The method of claim 23, wherein the donor fluorophore is a Green Fluorescent Protein and the acceptor fluorophore is a Red Fluorescent Protein.

32. The method of claim 23, wherein at least one of the first and second chemical entities comprises a streptavidin.

33. The method of claim 23, wherein one of the first and second chemical entities is a small molecule that becomes sterically hindered upon binding to the other of the first and second chemical entities.

34. The method of claim 23, wherein the donor fluorophore and the acceptor fluorophore are the same.

35. A method for detecting whether a FRET interaction is occurring between a first chemical entity in association with a donor fluorophore and a second chemical entity in association with an acceptor fluorophore, the method comprising:
exposing a region containing the fluorophores to radiation at an excitation wavelength for the donor fluorophore;
measuring a polarization anisotropy of a fluorescent signal at an emission wavelength for the acceptor fluorophore;
measuring a polarization anisotropy at the wavelength of a reference signal in the regions containing the fluorophores; and
comparing the measured anisotropies to determine whether a FRET interaction is occurring between the first and second chemical entities.

36. The method of claim 35, wherein the reference signal comprises radiation other than fluorescence of the donor fluorophore.

* * * * *